US010635785B2

United States Patent
Dempfle et al.

(10) Patent No.: US 10,635,785 B2
(45) Date of Patent: Apr. 28, 2020

(54) TO EXERCISE EQUIPMENT

(71) Applicant: INTEGRATED HEALTH PARTNERS LIMITED, London (GB)

(72) Inventors: Ulrich Dempfle, London (GB); Ratna Singh, London (GB); Oliver Bernath, London (GB)

(73) Assignee: INTEGRATED HEALTH PARTNERS LIMITED, London (GB)

( * ) Notice: Subject to any disclaimer, the term of this patent is extended or adjusted under 35 U.S.C. 154(b) by 548 days.

(21) Appl. No.: 15/323,876

(22) PCT Filed: Jun. 29, 2015

(86) PCT No.: PCT/GB2015/051887
§ 371 (c)(1),
(2) Date: Jul. 21, 2017

(87) PCT Pub. No.: WO2016/001637
PCT Pub. Date: Jan. 7, 2016

(65) Prior Publication Data
US 2017/0154165 A1 Jun. 1, 2017

(30) Foreign Application Priority Data

Jul. 4, 2014 (GB) .................................. 1411976.2

(51) Int. Cl.
*A61B 5/02* (2006.01)
*G06F 19/00* (2018.01)
(Continued)

(52) U.S. Cl.
CPC ...... *G06F 19/3481* (2013.01); *A61B 5/02405* (2013.01); *A61B 5/222* (2013.01);
(Continued)

(58) Field of Classification Search
USPC ................................................. 600/508–509
See application file for complete search history.

(56) References Cited

U.S. PATENT DOCUMENTS 6,059,692 A 5/2000 Hickman
6,601,016 B1 7/2003 Brown
(Continued)

FOREIGN PATENT DOCUMENTS

KR 100417108 B1 8/2003

OTHER PUBLICATIONS

Search Report received in European Patent Office application No. EP19175702 dated Nov. 22, 2019, 2 pages.
(Continued)

*Primary Examiner* — Christopher Koharski
(74) *Attorney, Agent, or Firm* — Blueshift IP, LLC; Robert Plotkin

(57) ABSTRACT

A control system for controlling one or more of a plurality of exercise apparatuses across a network comprises a processor; a communication subsystem configured to communication with the plurality of exercise apparatuses across the network; and memory for storing information about one or more users. The information comprises, for each user, identity information, including a user identifier; and a resistance level indicator. Upon receipt of a user identifier from an exercise apparatus in the network, the processor is configured to identify the resistance level indicator stored in the memory corresponding to the user identifier, and cause the communication subsystem to transmit to the exercise apparatus the resistance level indicator for that user. Upon receipt of a performance parameter of a user from an exercise apparatus in the network, the processor determines whether to modify the resistance level indicator of that user based on the received performance parameter.

15 Claims, 11 Drawing Sheets

(51) Int. Cl.
*G16H 20/30* (2018.01)
*A61B 5/024* (2006.01)
*A61B 5/22* (2006.01)
*A61B 5/00* (2006.01)
*A63B 21/012* (2006.01)
*A63B 22/06* (2006.01)
*A63B 24/00* (2006.01)
*A63B 71/06* (2006.01)

(52) U.S. Cl.
CPC ............ *A61B 5/746* (2013.01); *A63B 21/012* (2013.01); *A63B 22/0605* (2013.01); *A63B 24/0075* (2013.01); *A63B 24/0087* (2013.01); *A63B 71/0622* (2013.01); *A63B 71/0686* (2013.01); *G16H 20/30* (2018.01); *A63B 2024/0093* (2013.01); *A63B 2220/17* (2013.01); *A63B 2225/15* (2013.01); *A63B 2225/50* (2013.01); *A63B 2230/015* (2013.01); *A63B 2230/062* (2013.01)

(56) References Cited

U.S. PATENT DOCUMENTS

| | | | |
|---|---|---|---|
| 2005/0070809 A1 | 3/2005 | Acres | |
| 2005/0272561 A1 | 12/2005 | Cammerata | |
| 2006/0259275 A1 | 11/2006 | Maschke | |
| 2007/0033069 A1 | 2/2007 | Rao | |
| 2009/0258758 A1* | 10/2009 | Hickman | G06F 19/3481 482/8 |
| 2015/0360083 A1* | 12/2015 | Lagree | A63B 24/0075 482/130 |
| 2016/0317866 A1* | 11/2016 | Fung | A63B 24/0003 |

OTHER PUBLICATIONS

Anonymous, "High-Intensity Training," Wikipedia, May 26, 2014, XP055645783, Retrieved from the Internet, Nov. 22, 2019, 2 pages. <URL: https://en.wikipedia.org/w/index.php?title=High-intensity_training&oldid=610164365>.

* cited by examiner

FIG. 3A
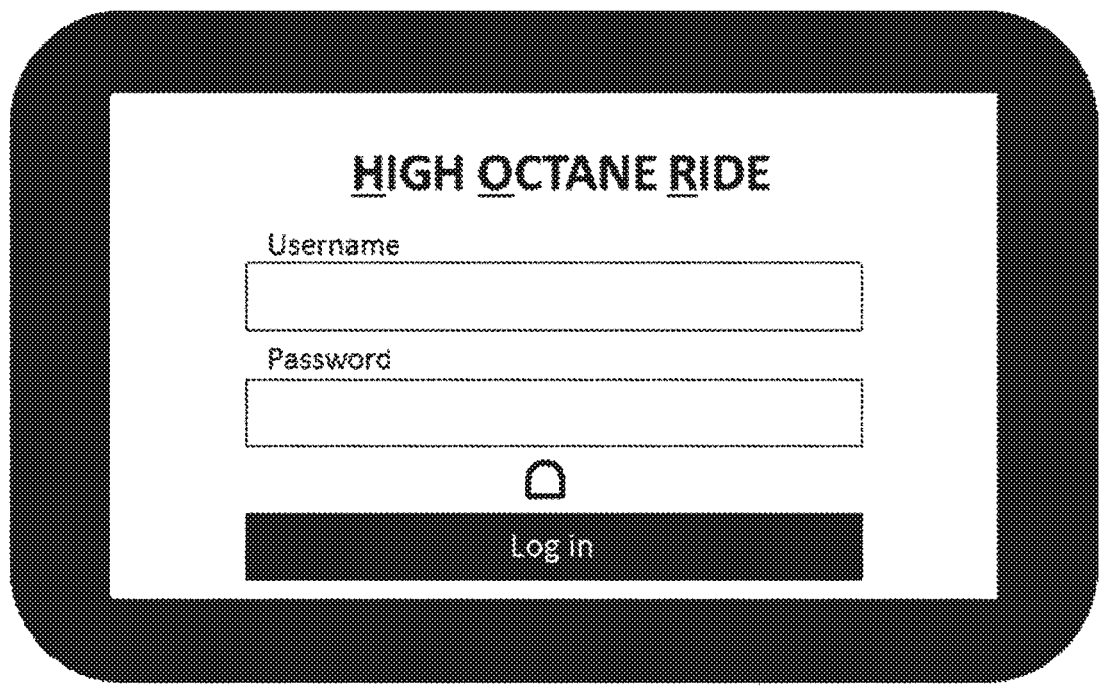
FIG. 3B

FIG. 3C
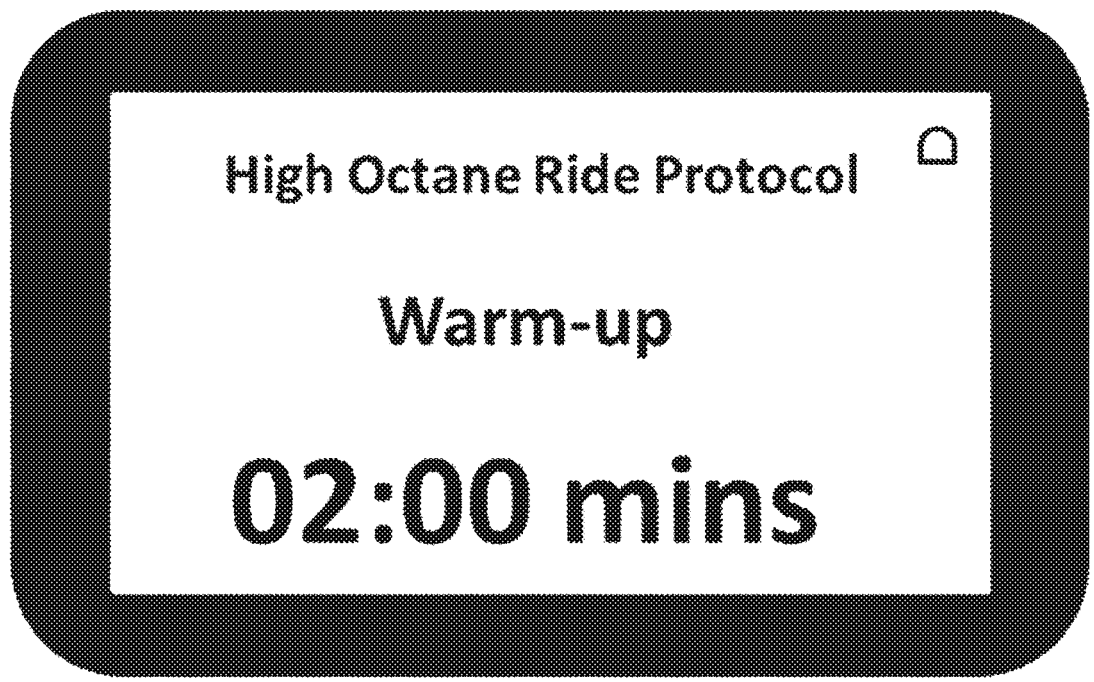
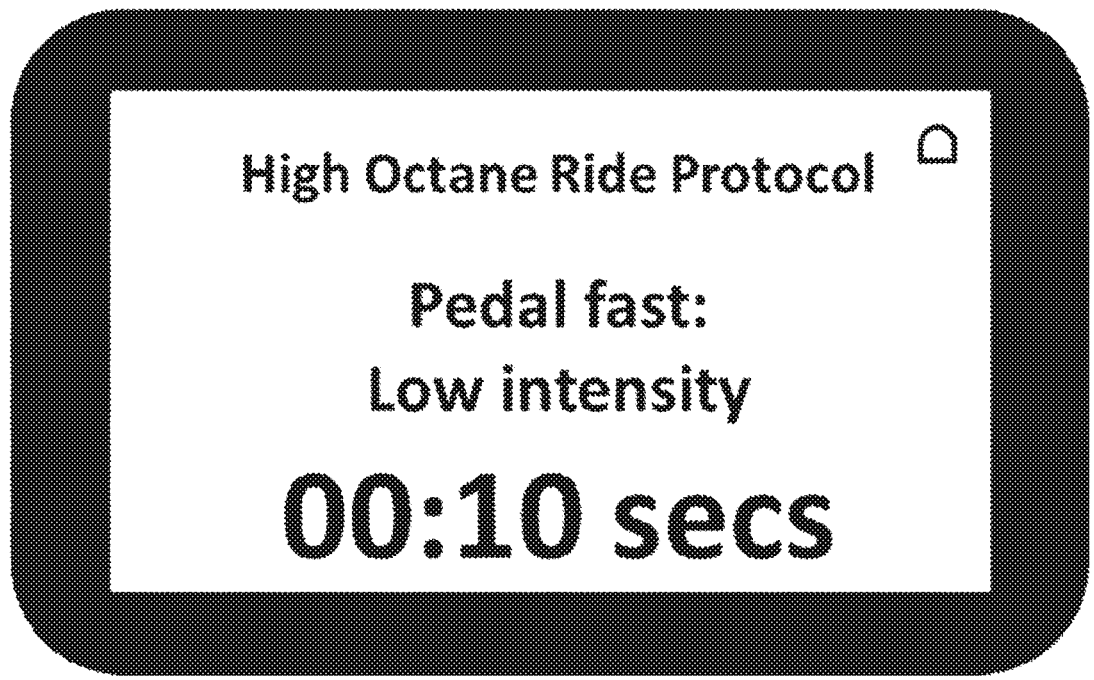
FIG. 3D

FIG. 3E
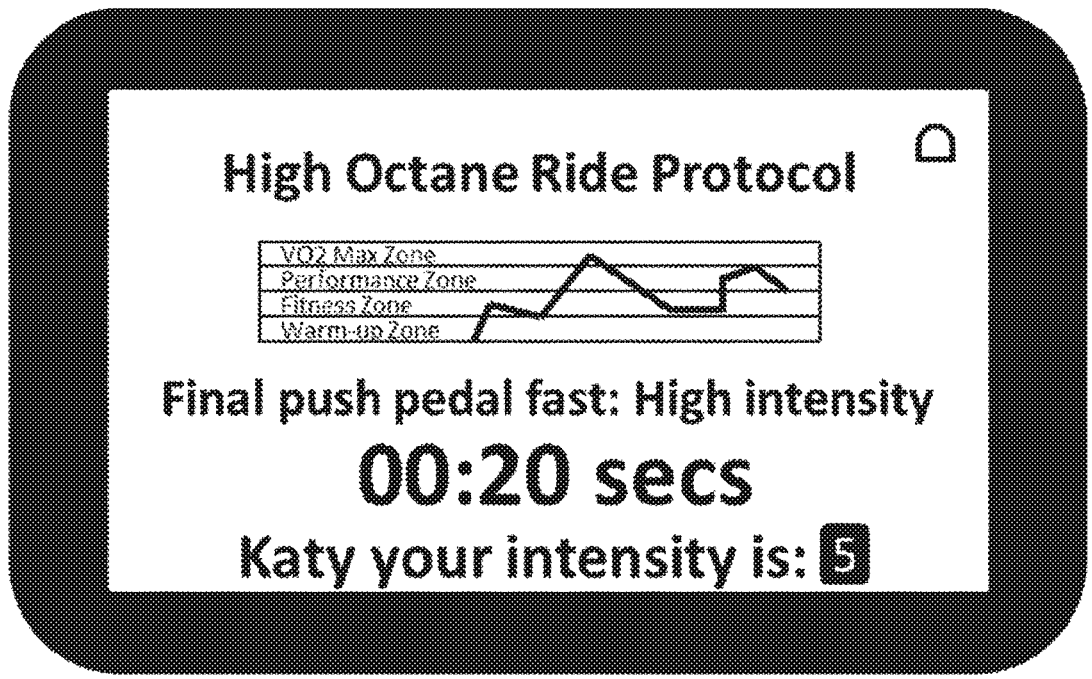
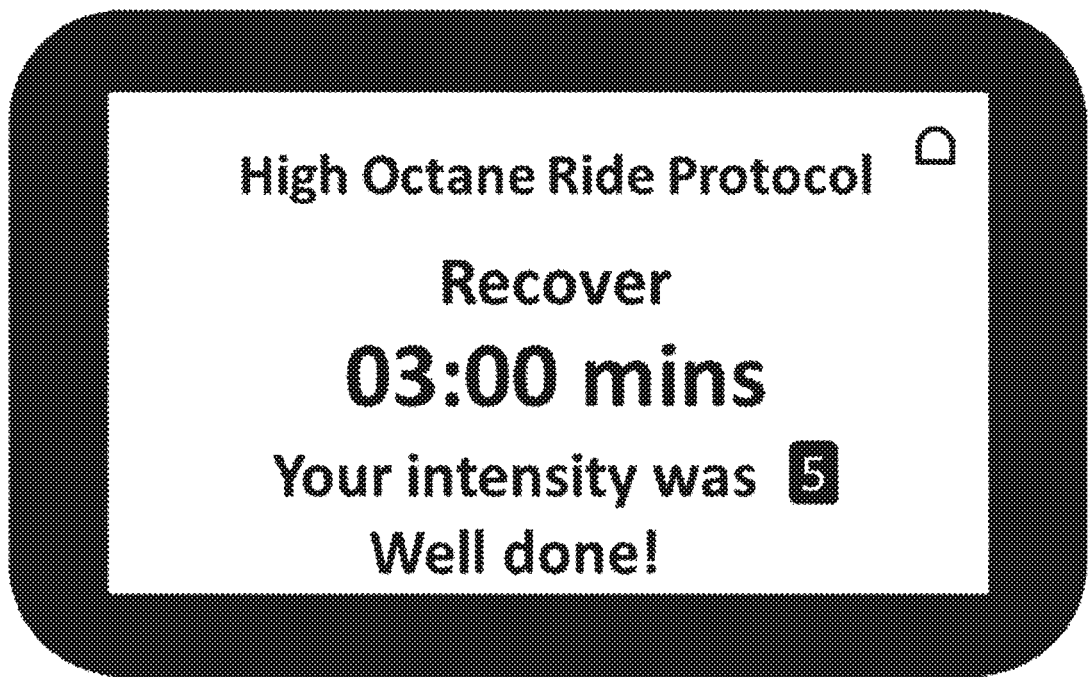
FIG. 3F

FIG. 3G
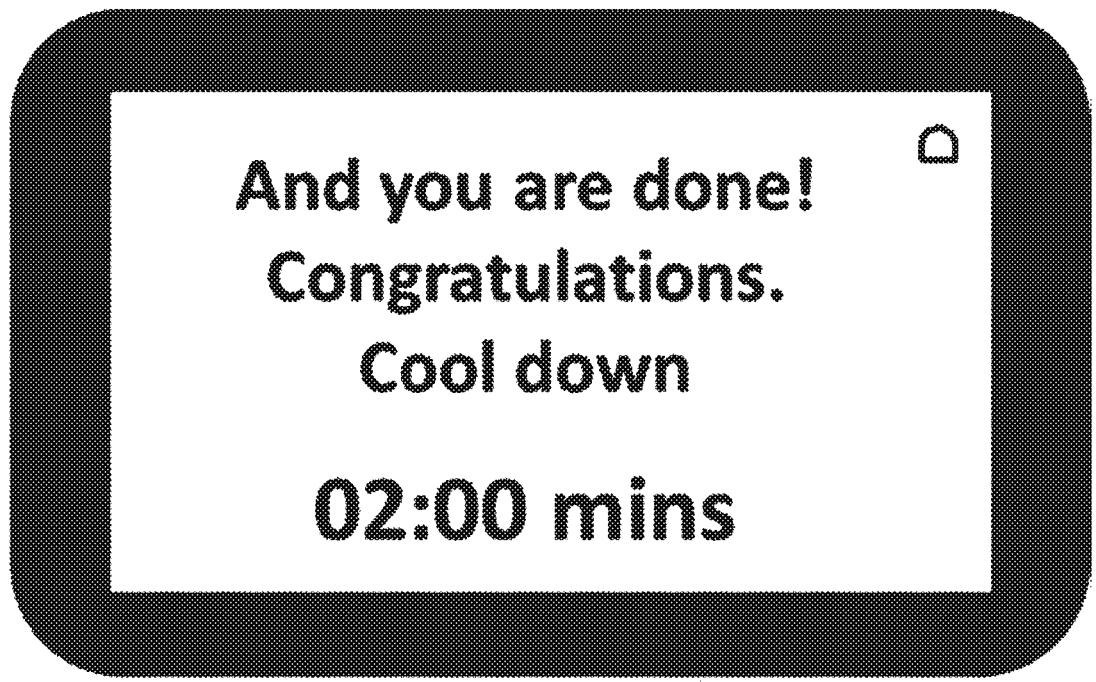
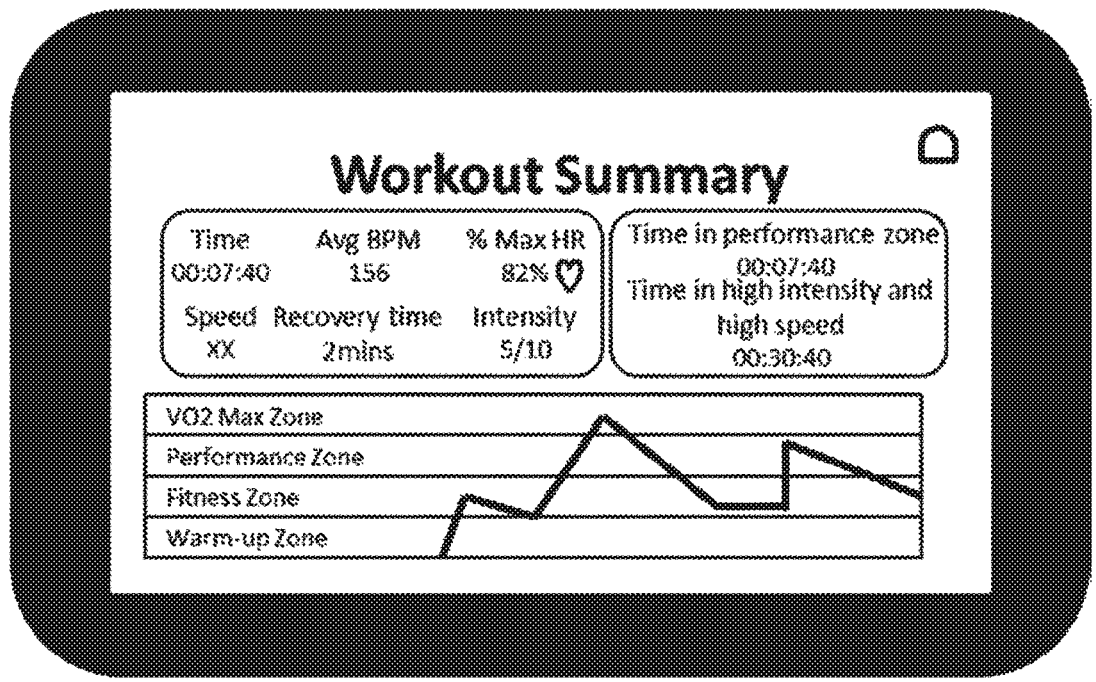
FIG. 3H

FIG. 3I
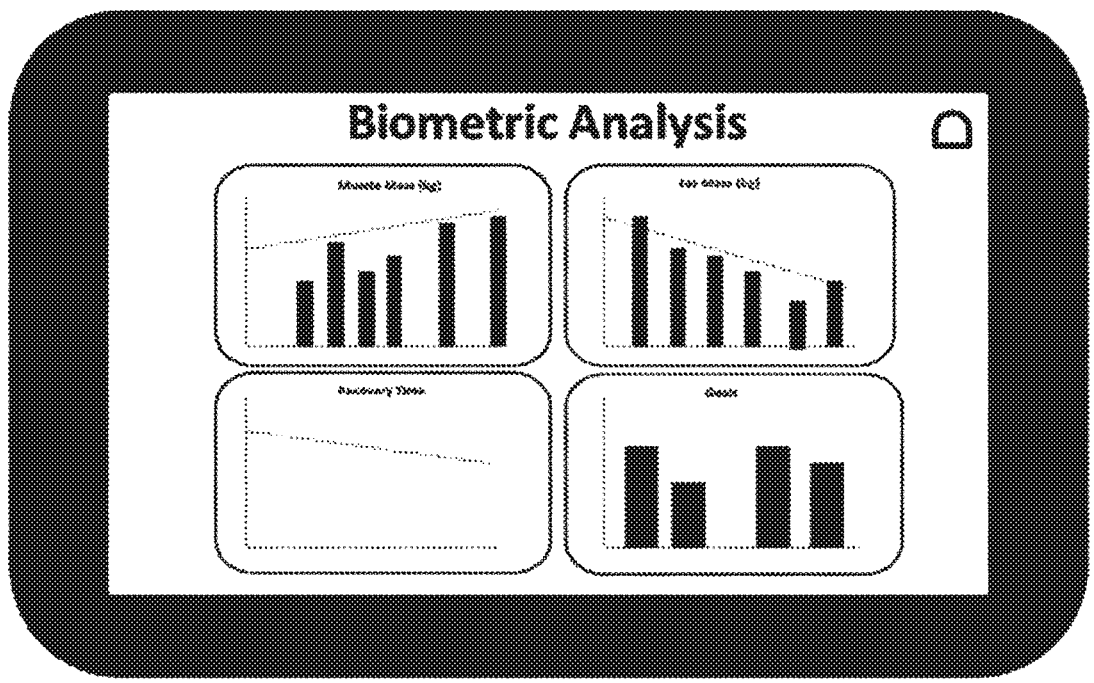
FIG. 3J

TO EXERCISE EQUIPMENT

FIELD

The invention generally relates to exercise apparatus and control systems thereof, and more particular to exercise equipment which facilitate the optimisation of exercise protocols performed on exercise apparatus.

BACKGROUND

High Intensity Training (HIT) is a form of exercise that has been proven in clinical trials to deliver the same, if not superior, benefits as traditional aerobic endurance exercise (such as jogging, walking, running, cycling) but in a shorter time. Some of the health benefits of HIT are improved cardiovascular fitness and improved sugar metabolism (better response to insulin and reduced risk of diabetes). The improved responsiveness of body cells to insulin also helps mobilising the body's fat stores when trying to lose weight.

HIT involves doing a small number of short intervals of exercise at very high intensity, which go beyond an individual's capacity to transport and use oxygen during exercise (i.e., $VO_2$max). For example, one HIT protocol consists of 3 minutes light warm-up cycling on an exercise bike at low resistance; followed by a 20 seconds sprint at high resistance for the exerciser to achieve maximal power output during the sprint; followed by a 3 minutes recovery period of slow cycling at low resistance; followed by a second high-intensity 20 seconds sprint at high resistance; followed by a 3 minutes cool-down period of slow cycling at low resistance. This protocol of under 10 minutes per exercise session performed 3 times per week has been scientifically proven under laboratory conditions to deliver the same benefits in terms of cardiovascular fitness ($VO_2$max) and sugar metabolism (insulin sensitivity) as four runs of 45 minutes each per week. Of course, the protocol may be varied in the number and duration of low resistance periods, and in the number and duration of peak performance protocols.

HIT is a well-established training method that has been known for some time. If the HIT exercise is carried our correctly, it represents a very effective and convenient workout in which users do not or only minimally sweat, which would allow the exercise to be carried out for, for example, at work without the need for changing clothes or having a shower.

However, there are currently no pieces of exercise apparatus on the market that have been specifically designed for HIT. For example, existing exercise bicycles are general purpose for multiple different kinds of exercise, and resistance levels thus need to be manually adjusted by the user, distracting the user from the focussed nature of the HIT workout. A range of different types of exercise apparatus are available for use in dedicated gyms, or at home, and some have been developed to include sophisticated control systems. For example, many gyms offer upright and reclining bikes, which are used for comparatively low intensity exercise. Many such bikes include pre-set programs, which a user may select to adjust resistance of the exercise over a period of time. These exercise bikes are not adapted to provide HIT exercise. If a user were to attempt to perform an HIT workout on existing bikes, they would have to input the resistance values for the workout themselves, with no guidance as to a correct value to choose.

To correctly carry out an HIT protocol, the user must exercise at very high intensity when required, and recover when required by exercising at low intensity. This is unfamiliar to many users, so, without apparatus specifically designed for HIT, it is likely that the user will not follow the HIT protocol correctly and not experience the full benefit of this form of exercise.

A user should be working at or near their maximum power output to correctly perform an HIT protocol; however it is known that maximum power output is not necessarily achieved at maximum resistance. In this regard, one significant problem which arises using standard exercise bikes is that many users perform the HIT protocol with too high or too low resistance levels, or with too high or too low cadence. Cadence is the rate of revolutions of the crank, i.e. the rate at which the cyclist is turning the pedals. It is particularly inconvenient for a user to adjust the resistance level manually, as this interrupts the user's exercise. It is also not advisable for the user to set their resistance level themselves, as this gives an additional distraction to the user. Furthermore, the user does not know what resistance level to choose, how to optimise their resistance level, and whether or not their resistance level should be changed depending on their performance. This uncertainty makes it difficult for a user to correctly carry out an HIT protocol on current exercise apparatus.

Another problem particularly associated with the difficult and intense nature of an HIT protocol is the motivation of the user. Enthusiasm and willpower are required to work at or near maximum intensity and power output. If the user is given the option to set their own resistance level they may start with too high a resistance, and then give up, or lower the level too far to give an easier workout, and thus not follow the protocol correctly. This is another reason to prevent the user from adjusting their resistance level.

Accordingly, there is a need for exercise apparatus that is specifically designed to make it easier for a user to correctly carry out an HIT protocol. This should involve minimal input from the user, and automatically optimise resistance levels such that the user is working at the correct intensity. If the input of the user at the start of each HIT protocol is minimised, the user will be more focussed on the protocol, and will therefore be more able to meet its particular exacting requirements, and thus see the full benefit of this form of exercise.

In addition, a problem associated with standard exercise apparatus is that it is unsuitable for use in public, or private areas other than gyms, such as office buildings, retail outlets, hotels, and so on. If conventional exercise apparatus was placed in public areas without supervision, there would be a significant risk of unauthorised and inappropriate use, which may put the user at risk of injury due to incorrect operation, overexertion, and so on. Furthermore, users may feel uncomfortable exercising on conventional bikes in public areas, particularly at peak performance levels, because they would feed exposed and would lack a minimum required level of privacy.

Health clubs and gyms normally offer a range of exercise bikes to conduct aerobic fitness exercises. However, this means that the exercise bikes are occupied by one individual user for a relatively long period of time. This makes it necessary to provide a greater number of pieces of expensive apparatus that occupy a larger floor space. Moreover, exercise bikes and other pieces of exercise equipment found in gyms are not specifically designed for HIT, and thus suffer the problems described above.

SUMMARY OF THE INVENTION

Accordingly, in a first aspect, the present invention provides a control system for controlling one or more of a plurality of exercise apparatuses across a network, each of the plurality of exercise apparatuses being configured to transmit a user identifier and a performance parameter of a user, the control system comprising:

a processor;

a communication subsystem configured to communication with the plurality of exercise apparatuses across the network; and memory for storing information about one or more users, the information comprising, for each user:
        identity information, including a user identifier; and
        a resistance level indicator;

wherein upon receipt of a user identifier from an exercise apparatus in the network, the processor is configured to identify the resistance level indicator stored in the memory corresponding to the user identifier, and cause the communication subsystem to transmit to the exercise apparatus the resistance level indicator for that user; and wherein upon receipt of a performance parameter of a user from an exercise apparatus in the network, the processor is configured to determine whether or not to modify the resistance level indicator of that user stored in the memory based on the received performance parameter.

The invention allows users to carry out a training session on a piece of exercise apparatus (such as an exercise bike) and follow a scientifically proven HIT protocol which is algorithmically optimised based on a measured performance parameter of the user. For the purposes of this description, a HIT protocol is a programme of activity defined by one or more periods in which the user exercises at high intensity against a particular resistance for a particular duration. The HIT protocol is chosen by the processing means based on biometric user information which is entered by or gleaned from the user, and is algorithmically optimised based on a measured performance parameter of the user performing the HIT protocol.

Further, this invention enables a piece of exercise apparatus (such as an exercise bike) to be situated outside of the conventional gym environment, such as in a public or private area (e.g., office buildings, retail outlets, gyms, or at home) and also to be operated safely unsupervised.

The control system allows for the provision of a plurality of apparatuses distributed across a building, town or country which are centrally controlled such that a user can use the apparatus at his or her convenience. The system associates a resistance level indicator with a user identifier, such that upon receipt of a user identifier (for example, when a user provides a unique access key or username and password specific to the user), the system is able to return the resistance level associated with that user. This can take place on any apparatus in the distributed network which is capable of communicating with the control system.

The resistance level indicator is used to set the resistance level of the apparatus used by the user. During exercise at that resistance level, the apparatus provides a performance parameter to the control system. This performance parameter reflects the performance of the user exercising at that resistance level. Upon receipt of the performance parameter, the control system determines whether or not to adjust the resistance level indicator of that user. If the performance parameter indicates that the user is performing the protocol too easily at a given resistance, the control system may determine that the resistance level indicator should be increased, and vice versa. Thus, the resistance level will be optimised for each individual user.

In a second aspect of the invention, the present invention provides an exercise apparatus configured to communicate with a remote server across a network, the remote server being configured to transmit a resistance level indicator indicative of a resistance level to be applied by the exercise apparatus, the exercise apparatus comprising:

a processor;

a communications subsystem configured to communicate with the remote server across the network;

an identification subsystem configured to receive a user identifier from a user;

a load for use in exercise and a brake for applying resistance to the load; and a measurement subsystem configured to measure a performance parameter of the user on the apparatus;

wherein upon receipt of a user identifier from a user, the processor is configured to cause the communication subsystem to transmit the user identifier to the remote server across the network;

wherein upon receipt of a resistance level indicator from the remote server, the processor is configured to cause the brake to apply a corresponding resistance to the load; and wherein upon measurement of a performance parameter of the user on the apparatus, the processor is configured to cause the communication subsystem to transmit to the remote server the performance parameter of that user.

For instance, one or more pieces of exercise apparatus according to the second aspect of the invention may be usable with the control system of the first in a distributed network.

It will be appreciated that the apparatus is able to receive a user identifier (such as a unique access key or username and password specific to the user) from the user, and transmit that identifier to the control system for use in retrieving the associated resistance level indication. The apparatus also provides a load movable by the user carrying out the exercise, and a brake which prevents the load from being moved, thereby offering resistance against the user's exercise. The resistance applied by the brake is dependent on the resistance level indicator received from the control system.

A third aspect of the invention provides an exercise apparatus comprising:

a processor;

a load for use in exercise and a brake for applying resistance to the load;

a measurement subsystem configured to measure a performance parameter of the user on the apparatus; and a data interrogation subsystem configured to access a memory for storing information about one or more users, the information comprising, for each user:
        a resistance level indicator; and wherein the processor is configured to cause the data interrogation subsystem to identify the resistance level indicator stored in the memory, and cause the brake to apply a corresponding resistance to the load; and wherein upon measurement of the performance parameter of the user on the apparatus, the processor is configured to determine whether or not to cause the data interrogation subsystem to modify the resistance level indicator of that user stored in the memory based on the measured performance parameter.

Thus, instead of distributing the system across a network, the invention could be practiced on one or more 'standalone' apparatuses, each of which is capable of accessing a resistance level indicator for a user, applying resistance corresponding to that indicator to a load (again, using a brake acting on the load), measuring a performance parameter of the user and based on the measured performance parameter, and determining whether or not to adjust the resistance level indicator.

In this case, the resistance level indicator could be stored in a memory on the apparatus (in which case, a user identifier may be necessary for retrieving the correct resistance level indicator), or the indicator could be stored in a device supplied by the user (such as a fob or smartphone), in which case no such user identifier would be necessary.

Hence, in a preferred implementation of the third aspect of the invention, the apparatus further comprises an identification subsystem configured to receive a user identifier from a user;

wherein the information about one or more users further comprises, for each user, identity information including a user identifier; and wherein upon receipt of a user identifier from the user, the processor is configured to cause the data interrogation subsystem to identify the resistance level indicator stored in the memory corresponding to the user identifier.

This enables a plurality of users to use the same bike, each of whom could access their own resistance level indicator stored locally on the machine, and thus remove the need to carry a device supplied by the user.

Further optional features of the first to third aspects of the invention are given below. Methods corresponding to the first to third aspects are also contemplated.

In particular, in a fourth aspect of the invention, there is provided method for controlling one or more of a plurality of exercise apparatuses across a network, the method comprising:

receiving a user identifier from an exercise apparatus;
retrieving a resistance level indicator corresponding to the user identifier from a memory;
transmitting the resistance level indicator to the exercise apparatus;
receiving a performance parameter from the exercise apparatus;
determining, based on the received performance parameter, whether or not to modify the resistance level indicator; and, if the determination is positive:
modifying the resistance level indicator corresponding to the user identifier in the memory.

In a fifth aspect of the invention, there is provided a method of controlling an exercise apparatus comprising:

receiving a user identifier from a user;
transmitting the user identifier to a remote server across a network;
receiving a resistance level indicator from the remote server;
applying resistance to a load for use in exercise by causing a brake to apply a resistance corresponding to the received resistance level indicator to the load;
measuring a performance parameter of the user on the apparatus; and
transmitting the measured performance parameter to the remote server In a sixth aspect of the invention there is provided a method of controlling an exercise apparatus, the method comprising:

accessing from a memory a resistance level indicator of the user;
applying resistance to a load for use in exercise by causing a brake to apply a resistance corresponding to the retrieved resistance level indicator to the load;
measuring a performance parameter of the user on the apparatus;
determining whether or not to modify the resistance level indicator of that user based on the measured performance parameter; and, if the determination is positive:
modifying the resistance level indicator in the memory.

Optional features for the fourth to sixth aspects of the invention correspond to the optional features of the first to third aspects, as described below.

Preferably, the information about one or more users further comprises, for each user, biometric information; and wherein the processor is further configured to set the resistance level indicator of the user based on the user's biometric information.

Hence, in situations where it is inappropriate or impossible for the system or bike to modify an existing resistance level indicator (for instance, because one does not exist, or has not been modified for a predetermined period of time), the indicator may be set based upon biometric information. This could be weight, height, body mass index (BMI), fat content, muscle mass or any other physiological or biometric information, but is preferably weight.

Preferably the processor of the system or bike sets the resistance level indicator of the user based on the user's biometric information according to a look-up table. This is a convenient and accurate way of associating a resistance level indicator to particular biometric information.

Preferably, the information about one or more users further comprises, for each user, a counter indicative of the number of exercises completed by the user. This enables the system or bike to keep track of how many exercises have been performed previously so as to judge (for example) whether or not to set a resistance level indicator based on biometric information, or to determine whether or not modify an existing resistance level indicator based on a performance parameter.

For instance, the processor may be configured to set the resistance level indicator of the user based on the user's biometric information only when the counter is equal to or below a threshold value, such as 2. In that case, the processor will set the resistance level indicator based on a biometric information for the first three exercises (when the counter is at 0, 1 and 2), but not afterwards. It may be possible to reset the counter if, for example, the user has not exercised for a predetermined period of time.

Optionally, the processor may be configured to apply a multiplier to the biometric information according to the value of the counter. This enables the resistance level indicator to be set as a proportion of its look-up table value, which is helpful in certain circumstances. For instance, whist the user is getting used to the exercise, it is helpful to provide 'ramp up rides' to build the user up to the final look-up table value.

For instance, the processor may be configured to: apply a multiplier of 0.6 to the biometric information when the counter is equal to 0; and/or apply a multiplier of 0.8 to the biometric information when the counter is equal to 1; and/or apply a multiplier of 1 to the biometric information when the counter is equal to 2.

The system or bike need not only transmit and receive a resistance level indicator. For instance, the processor may be further configured to transmit to the exercise apparatus (or receive from the control system) instructions for implementing an exercise protocol. An exercise protocol is a well understood fitness programme to be carried out on a piece of equipment. The protocol comprises a plurality of periods of a certain duration, during which different qualities of exercise are implemented. For instance, the protocol may include first and second sprint periods, during which the user should sprint. Other qualities of exercise include gradients, speeds, weight, and so on.

The protocol preferably comprises applying at least two different resistance levels during the plurality of periods. Optionally, the resistance level remains constant throughout any period.

An exemplary protocol consists of: a warm up period, followed by a first sprint period, followed by a first recovery period, followed by a second sprint period, followed by a second recovery period.

Preferably in such a protocol, the duration of the warm-up period is 180 seconds; the duration of the first sprint period is 20 seconds; the duration of the first recovery period is 180 seconds; the duration of the second sprint period is 20 seconds; and the duration of the second recovery period is 180 seconds.

In a particularly preferred embodiment, the resistance level applied during the first and/or second sprint periods is based on the resistance level indicator. In other words, the resistance which is set by the resistance level indicator stored by the control system or the bike is used only during one or both 'sprint' periods, where the user is working hardest during the whole exercise.

For instance, a first resistance level is applied during the warm up period; a second resistance level is applied during the first sprint period; the first resistance level is applied during the first recovery period; the second resistance level is applied during the second sprint period; and the first resistance level is applied during the second recovery period.

The first resistance level may be zero, or may be a non-zero level which is the lowest resistance setting of the exercise apparatus.

The performance parameter is preferably a ratio of a first performance measurement to a second performance measurement, wherein the first and second performance measurements are taken at different times during an exercise. In this way, the performance parameter acts as a measurement of how quickly and by how much a user's performance worsens over time (i.e. how much harder a user is finding the exercise at different stages). Thus, the first performance measurement is preferably taken before the second performance measurement.

Preferably, the first and second performance measurements are taken during the second sprint period, which is the optimal time for the user's performance to be measured, since the user is most likely to exhibit his or her most significant worsening of performance during this period.

Preferably the first performance measurement is taken 5 seconds into the second sprint period, and more preferably the second performance measurement is taken 15 seconds into the second sprint period. Hence, where the second sprint period is 20 seconds long, the user's performance is measured 5 seconds into the sprint (when the user would be performing comparatively well) and 5 seconds from the end of the spring (when the user would be performing comparatively poorly).

The processor is preferably configured to compare the received performance parameter with one or more threshold values to determine whether or not to modify the resistance level indicator. For instance, where the performance parameter is a ratio, there may be an upper threshold (of 0.75, for instance), above which the processor causes the resistance level indicator to be increased. In other words, if the performance of the user does not drop by at least 25% over the two measurements, the resistance level of the user's next exercise will be greater.

In such an optional embodiment, the processor may be further configured to compare the received performance parameter with an upper threshold value, and to increase the resistance level indicator if the received performance parameter exceeds the upper threshold values.

Likewise, there may be a lower threshold (of 0.5, for instance), below which the processor causes the resistance level indicator to be decreased. In other words, if the performance of the user drops by more than half across the two measurements, the resistance level of the user's next exercise will be less.

In such an optional embodiment, the processor may be further configured to compare the received performance parameter with a lower threshold value, and to decrease the resistance level indicator if the received performance parameter is below the lower threshold value.

The processor may be further configured to compare the received performance parameter with an upper threshold value and a lower threshold value, and to maintain the resistance level indicator if the received performance parameter is between the upper and lower threshold values.

Upon reaching a determination to modify the resistance level indicator, the processor may be configured to modify the resistance level indicator by a predetermined amount. This could be fixed in all cases, or vary, depending on the preferred implementation. For instance, the amount by which the resistance level indicator is modified could depend on the magnitude of the performance parameter; it could be modified by a relatively large amount if the performance parameter is very positive or negative, for example, and modified by a relatively small amount if the performance parameter is only slightly positive or negative.

In the case where the performance parameter exceeds the aforementioned upper threshold, the processor may be configured to increase the resistance level indicator by said predetermined amount (optionally depending on magnitude of the performance parameter) and in the case where the performance parameter falls below the aforementioned lower threshold, the processor may be configured to reduce the resistance level indicator by said predetermined amount (optionally, again. depending on magnitude of the performance parameter).

The resistance level indicator may be a value between 0 and 255. This is particularly advantageous since it can be stored using just 8-bits of information, which is convenient for data processing. In this case, the predetermined amount by which the level may vary is 1 (i.e. $\frac{1}{256}$th of the total range of resistance), although it could be 2, 5, 10 or any number.

The performance parameter may optionally include the heart rate of a user. The heart rate can be monitored by suitable components on the bike or control system, and the respective processor may be further configured to cause the communication subsystem to transmit an alert to the exercise apparatus (or display a warning on or cease operation of the exercise apparatus) if the heart rate exceeds a predetermined threshold. This enables suitable safety precautions to be implemented on the exercise equipment.

Preferably, the exercise apparatus is an exercise bike, in which case performance parameter is preferably revolutions per minute RPM. Exercise bikes are particularly convenient for practising HIT, and RPM can be used to calculate power, which is the best measure for optimising performance.

Preferably the data interrogation subsystem or user identity subsystem of the exercise apparatus further comprises one or more of a dock for receiving a removable storage device; a card reader for receiving an identity card; and an electronic login system for accepting an electronic login. Other means for supplying identity information, including a user identifier are also possible.

Where the exercise apparatus calls for memory on which to store a resistance level indicator, the memory may form part of a removable storage device insertable into the dock by the user.

The exercise apparatus may be configured such that the processor causes the apparatus to be inoperable until the processor receives a valid user identifier from the user. For instance, the processor could cause the brake to apply so great a resistance to the load that the apparatus is 'locked', until valid credentials have been supplied.

Preferably the resistance applied by the brake during exercise is not adjustable by the user during exercise. Whilst the user may have access to an emergency stop to cease exercise altogether (by applying enough resistance to stop the load from moving altogether, for instance) adjustment of the resistance mid-exercise is ideally prohibited to ensure the user completes the HIT as intended. Thus, the equipment is superior to general purpose equipment often found in gyms, for example, which are often not used as effectively as they could be.

Optionally, the resistance applied by the brake during exercise is controllable only by the resistance level indicator stored in the memory.

Preferably the exercise apparatus further comprises a screen at least partially enclosing the apparatus to enable the user to exercise with a suitable degree of privacy. The exact configuration of the screen will depend on the preferred implementation, but it could be separate from or integral with the exercise equipment.

BRIEF DESCRIPTION OF THE DRAWINGS

Embodiments of the invention will now be described in detail, with reference to the accompanying drawings, in which:

FIGS. 3A to 3J show screenshots of a display of the exercise apparatus shown in FIG. 2 during an exercise;

DETAILED DESCRIPTION OF THE INVENTION

The embodiments below are exercise bikes, which are found to be particularly effective at delivering HIT. It will be understood, however, that the invention is not limited only to exercise bikes, and may be applied to alternative forms of exercise apparatus, such as rowing machines, elliptical machines or X trainers, climbing machines, stair machines, or any apparatus where a resistance is applied and can be varied, and where performance is measurable.

Figure 1:
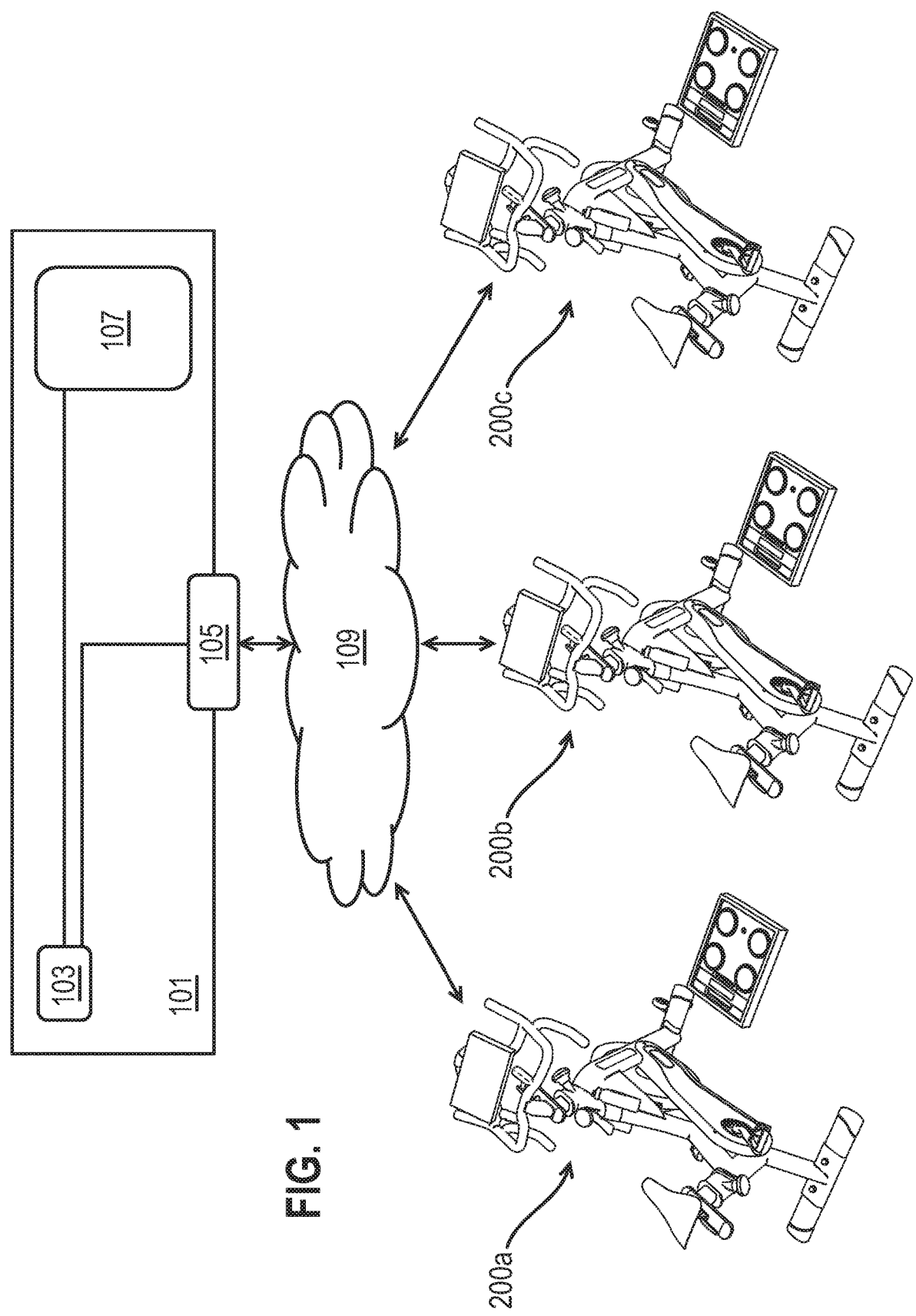
FIG. 1 shows a schematic of a control system according to an embodiment of the first aspect of the invention in communication with a plurality of bikes according to the second aspect of the invention.

FIG. 1 shows a schematic of a control system 101 of the first aspect of the invention. The control system comprises a processor 103, a communication subsystem 105, and a memory 107.

The control system 101 is in communication with a plurality of exercise bikes 200a-200c across a network 109, via the communication subsystem 105. The network is a wide area network (WAN) wherein the plurality of exercise bikes 200a-200c communicate with the control system 101 wirelessly, but the network could be a local area network (LAN), and each of bikes 200a-200c may be wired to the control system 101 or communicate with the control system 101 wirelessly, and may use any known communication protocol such as email, http, ftp, over any transmission medium including Bluetooth, GPRS, 3G or 4G.

The memory 107 is a hard disk, but may be any suitable memory for storing data. The memory 107 is configured to store user data, including information about a plurality of users of the exercise equipment. This information includes, for each user, identity information including a user identifier which is unique to the user to enable the user to be identified. The identity information may also include name, address, gender, age, and any other information which is desirable to record about the user. The information further includes, for each user, biometric information including the weight of the user. The biometric information may also include muscle mass, percentage of fat, water content, height, body mass index (BMI), and any other biometric information which is desirable to record about the user. The information further includes, for each user a resistance level indicator which sets the resistance level to be applied by the exercise bikes for that user (as described below). The information may further include additional details of exercise protocols to be implemented by the exercise bikes, depending on the preferred implementation.

Figure 2:
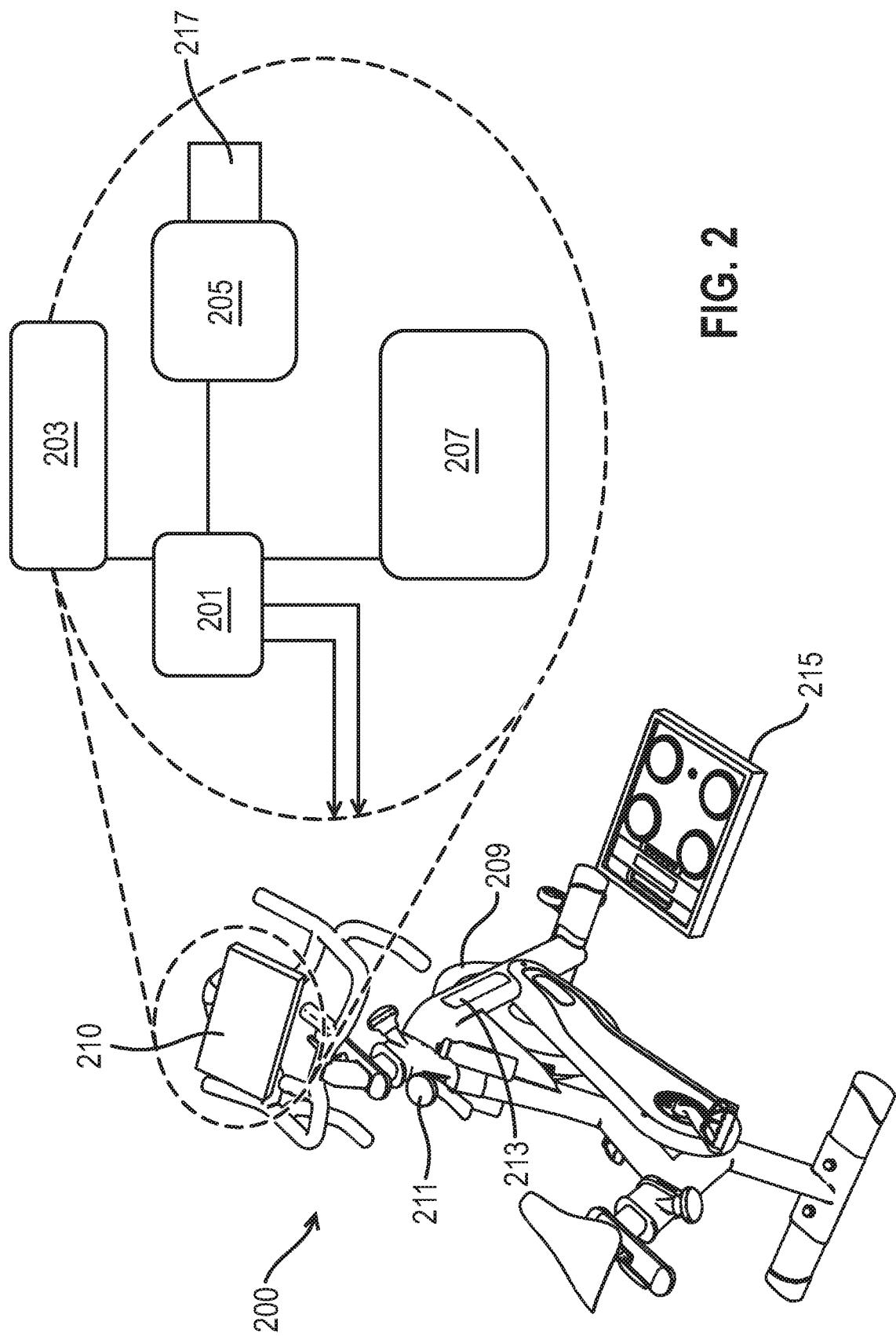
FIG. 2 shows a schematic of one of the exercise apparatuses shown in FIG. 1.

FIG. 2 shows a schematic of one of the exercise bikes 200 shown in FIG. 1, and according to the second aspect of the invention.

The exercise bike may be a commercially available exercise bike suitable for sprint training (such as the X-1000 bike manufacture by Trixter™, or the Spinner™ NXT bike manufactured by StarTrac™, for example), but any suitably modified conventional exercise bike will suffice. A skilled person is familiar with the arrangements of such readily available exercise bikes and so no further description is required here.

In other embodiments, the exercise bike may be designed specifically for HIT protocols. Such a bike may have a number of bespoke components. For instance, the bike frame structure may be engineered to withstand high intensity exercises reaching power outputs of 1,500 watts and above. Conventional frames are designed for maximum power outputs of 800 watts. The bike may be provided with a magnetic brake system with motor controlled magnet position. Such a system allows resistance to be increased rapidly—within 1 second, for example, which is beneficial for HIT exercise protocols. Conventional motor-driven magnetic brake systems are not able to adjust brake resistance so rapidly. The bike may be provided with a toothed belt, which avoids the risk of slippage of transmission from crank pulley to flywheel at high power outputs. Conventional belt-driven exercise bikes use poly-V belts, which would slip at power output levels of about 1,000 watts and above when resistance is applied suddenly.

The exercise bike comprises computing means 210 in the form of a tablet computer (although other means are possible). The tablet comprises a processor 201, a communication subsystem 203, an identification subsystem 205 and a display 207.

The exercise bike further comprises a load 209 in the form of a flywheel, which the user rotates by applying force to pedals, as is well-understood. The exercise bike further comprises a brake 211 for applying resistance to the flywheel to varying the force which the user must apply to the pedals to rotate the flywheel. The brake 211 acts on the flywheel 209 to increase the effort required for a user to rotate the flywheel 209. The brake is configured to apply resistance ranging from no resistance to a maximum resistance such that the flywheel is locked from rotation. The brake physically contacts the flywheel to impart resistance, but any other suitable arrangement may be provided, such as hydraulic or magnetic braking systems. Where the exercise equipment is not a bike, a skilled person will understand that equivalent loads and brakes for applying resistance to the load can be implemented.

The exercise bike further comprises a measurement subsystem 213 configured to measure a performance parameter of the user on the apparatus, in this case the revolutions of the flywheel or pedals per minute (RPM). Measurement of other performance parameters (such as force applied to the pedals, heart rate, etc.) is also possible.

Coupled to the computing means 210 of the bike 200 is a biometric scale 215. The user's biometric information may be obtained using the scale, which may be sent to the computing means. A suitable biometric scale which is available commercially is the Tanita SC-240 body composition analyser, although any suitable scale may be used. Any other suitable means for receiving, measuring, or otherwise gleaning biometric information from the user may be used in addition to or in replacement of the biometric scale. Preferably, the scale or other means is able to obtain one or more of the following pieces of biometric data: weight, muscle mass, percentage of fat, water content, height, body mass index (BMI).

The identification subsystem comprises a dock 217 for receiving a key fob inserted by a user containing that user's user identifier in the form of an alphanumeric code stored on the fob. It will be appreciated that the user identifier could take other forms. For instance, the tablet computer may be adapted to permit a user to provide the user identifier to log-in to the exercise bike system to begin an exercise. Users may be prompted to identify themselves by inputting a username and/or password; by the use of an RFID chip; a smartphone app; a fingerprint; a removable memory device; or any other variety of standard methods of such, as will be well understood by the skilled person.

However the user identifier is received, the processor 201 causes the communication subsystem 203 to transmit the user identifier to the control system 101 across the network 109. The user identifier corresponds to a user identifier stored in memory 107, and the control system is thus able to access the information associated with that user.

The processor 201 is coupled to the brake 211 to cause the brake 211 to apply a resistance to the flywheel 209. With the exception of safety controls such as an emergency stop, the user is unable to manually adjust the resistance applied by the brake 211 to the flywheel 209 manually or to control the processor so as to cause it to adjust the resistance. Additionally, the processor is configured to apply a resistance to prevent the bike from being operated (i.e. to prevent the flywheel from rotating) without a registered user being logged in to the system.

The processor is coupled to the measurement subsystem 213, which includes at least one sensor (not shown) for sensing RPM. For example, one or more sensors may be positioned on the frame adjacent the flywheel to sense flywheel rotation speed; one or more sensors may be positioned on the frame adjacent the pedals to sense cadence. All such sensors could be arranged by a skilled person as necessary to determine performance of the user during an exercise.

In preferred implementations, the processor may be adapted to measure or receive, compute and display cadence, power, pedal pressure, heart rate, and timing during an exercise. The heart rate may be measured via one or more electrodes located at the handle bar, or wirelessly via a wrist or chest strap capable of measuring heat rate. The processor may cause the display 207 to show the measured performance parameters, and also to show instructions to users during the HIT exercise, as explained in more detail below with reference to FIGS. 3A to 3J.

Figure 4:
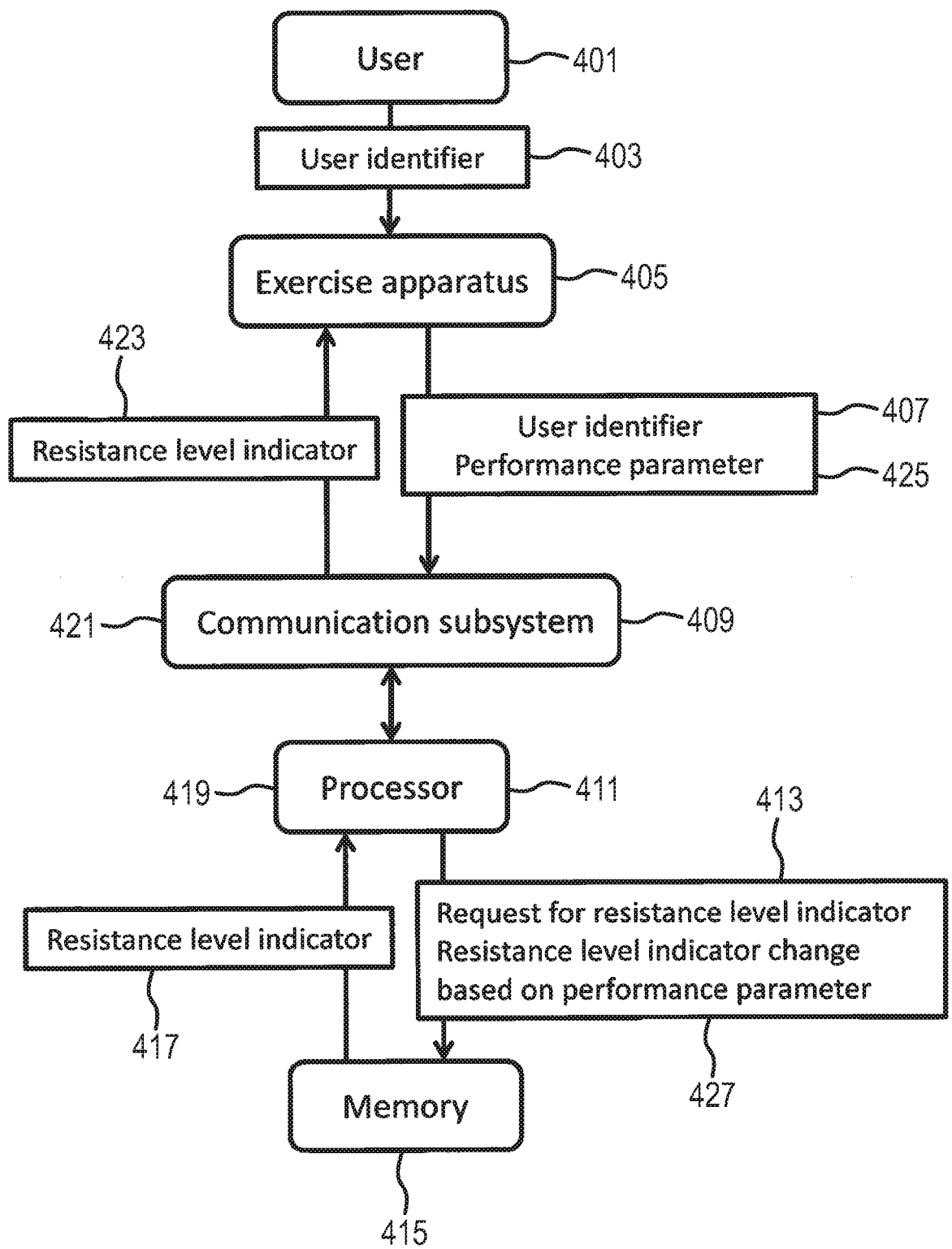
FIG. 4 shows a flow diagram of a method of operating the control system and exercise equipment shown in FIG. 1.

In use (and with reference to the process illustrated in FIG. 4), the control system 101 and exercise bike 200 operate as follows. A user mounts the bike (step 410) and provides the exercise bike 200 with his or her user identifier (step 403) in the form of a key fob (not shown) inserted into the dock 217. The bike processor 201 interrogates the fob and receives the user identifier (step 405), and then causes the communication subsystem 203 to transmit the user identifier to the control system 101 across the network 109 (step 407).

The user identifier is received at the communication subsystem 105 of the control system 101 (step 409) and the control system processor 103 processes the received user identifier (step 411), and interrogates the memory 107 (step 413) to retrieve information about the user corresponding to the user identifier (step 415). This information includes, at least, a resistance level indicator (step 417).

The control system processor 103 then processes the resistance level indicator (step 417) and causes the communication subsystem 105 to transmit the resistance level indicator associated with that user to the bike from which the corresponding user identifier was received (step 419).

The resistance level indicator is received at the communication subsystem 203 of the bike 200 (step 423) and, at some point during the user's exercise, the bike processor 210 causes the brake 211 to apply a level of resistance to the flywheel according to the resistance level indicator (as explained in more detail below).

During the user's exercise, the bike processor 210 causes the measurement subsystem to measure a performance parameter of the user, including at least the RPM. The bike processor 210 then causes the communication subsystem to transmit the performance parameter to the control system 101 across the network 109 (step 425).

The performance parameter is received at the communication subsystem 105 of the control system 101 and the control system processor 103 carries out a computation (described in more detail below) to determine whether or not to modify the resistance level indicator based on the received performance parameter. If the determination is positive, the processor modifies the resistance level indicator stored in memory (step 427).

Determination of whether to modify the resistance level indicator takes place once per exercise, and not continuously during the exercise. Thus, where the resistance level indicator stored in memory is modified based on the performance parameter measured during one exercise, the modified resistance level indicator will be used to set the resistance applied by the brake for the next exercise.

The control system 101 and bike 200 are configured such that a user's exercise is performed according to an exercise protocol. Either the protocol can be entirely configured by the control system 101 and transmitted to the bike 200 along with the resistance level indicator, or the protocol can be preconfigured to some extent such that certain invariable aspects are stored on the bike, whilst variable aspects (including the resistance level indicator) are transmitted from the control system 101 to the bike.

A protocol is defined by a plurality of periods of a certain duration, during which different qualities of exercise are implemented. For instance, the protocol may include first and second sprint periods, during which the user should sprint. Other qualities of exercise include gradients, speeds, weight, and so on. A preferred protocol is as follows:
1. a warm up period of 180 seconds where a first resistance level is applied; followed by
2. a first sprint period of 20 seconds where a second resistance level is applied, the second resistance level being based on the resistance level indicator associated with the user; followed by
3. a first recovery period of 180 seconds where the first resistance level is applied again; followed by
4. a second sprint period of 20 seconds where the second resistance level is applied again; followed by
5. a second recovery period where the first resistance level is applied for the final time.

In this case, the exercise bike 200 is preconfigured to implement the five different periods of the specified duration, and is furthermore preconfigured to apply the first resistance level (of low or zero resistance) during the warm up, and first and second recovery periods. The only information not preconfigured on the exercise bike 200 is the second resistance level that is based on the resistance level indicator associated with the user, which is received from the control system 101. However, other embodiments may use different preconfigurations on the exercise bike 200, and configure the control system 101 to transmit any information not so preconfigured.

The above protocol is an example of a preferred protocol, where the resistance level indicator defines the second resistance level (i.e. the resistance level used during the high intensity sprint sections of the HIT protocol). It will be understood that other protocols may be used. For example, the number and duration of the sprint and recovery periods may be changed; different resistance levels may be used for different sprints; a constant resistance level may be used for the whole protocol; or other such variations. Another option would be to have a protocol comprising three 20-second sprints, or to have a protocol comprising 30-second sprints. The first resistance level may be the lowest resistance setting of the exercise apparatus, or some other low value such that it does not cause undue exertion to the user.

The HIT protocols may differ depending on the weight of the user (or other biometric user information such as muscle mass, BMI, height, etc.). Alternatively, the same format of HIT protocol (i.e. with the same timings of the high and lower intensity sections of the protocol), may be suitable for all users.

If multiple HIT protocols are stored, the tablet may automatically select the appropriate HIT protocol for an individual user based on biometric user data. This could be the user's weight or alternatively other biometric information such as the user's muscle mass, BMI, height, etc.

The control system and bike according to the invention optimise the resistance level indicator for each individual user. Thus, for the exemplary HIT protocol given above, the resistance level used during the high intensity sprint sections is optimised for each user. This is based on a measured performance parameter of the user when performing the HIT protocol.

Whilst the user carries out the HIT protocol (whatever form it takes), and the exercise bike 200 measures a performance parameter (in the exemplary case, RPM) of the user. This parameter is then transmitted to the control system 101 and used to determine whether or not to modify the resistance level indicator of that user stored in the memory, as described above.

A particularly preferred performance parameter is a ratio of two performance measurements taken at different times during the exercise. In the present case, the bike measures the RPM at two points in the second sprint and calculates a ratio of the second measurement to the first to provide a measure of the decrease in performance in that second sprint period. The first measurement ($RPM_5$) is taken 5 seconds in to the second sprint period (i.e. 385 seconds in to the exercise according to the above protocol) and the second measurement ($RPM_{15}$) is taken 15 seconds in to the second sprint period (i.e. 395 seconds in to the exercise according to the above protocol). Based upon the two measurements the ratio $RPM_{15}:RPM_5$ is calculated.

Either the exercise bike 200 can transmit both performance measurements ($RPM_5$ and $RPM_{15}$) to the control system 101, or the exercise bike 200 can calculate the aforementioned ratio and transmit that.

Upon receipt of the performance parameter (either the ratio or performance measurements), the processor 103 of the control system 101 determines whether or not to adjust the resistance level indicator stored in memory 107 for that user by comparing the ratio to threshold values and adjusting the resistance level indicators accordingly.

For instance, in the present case, the processor 103 applies the following logic statements to the performance parameter:
if $[RPM_{15}/RPM_5>X]$ then increase the resistance level indicator by Z; else
if $[RPM_{15}/RPM_5<Y]$ then reduce resistance level indicator by Z; else
do not adjust the resistance level indicator In the exemplary case, X is 0.75 and Y is 0.5, but these values may be adjusted or other values may be used instead.

In the exemplary case, the resistance level indicator takes values from 0-255 and Z is 1, but these values may be adjusted or other values may be used instead. For instance, Z may be a percentage of the current resistance level indicator.

According to the algorithm above, if the user's performance during the second sprint decreases by less than 25% between 5 seconds and 15 seconds (i.e. the resistance is too low such that the user does not have to work hard enough to maintain their RPM to perform the exercise adequately), then the resistance level indicator will be increased. On the other hand, if the user's performance during the second sprint decreases by more than 50% between 5 seconds and 15 seconds (i.e. the resistance is too high for the user to maintain their RPM to perform the exercise adequately), then the resistance level indicator will be decreased.

If the ratio falls between the values X and Y, then the resistance level indicator is already optimised and remains unchanged. The values X, Y, and Z may be varied by the administrator of the exercise protocols and apparatus.

It will be understood that by applying the algorithm above, the resistance level of the exercise apparatus may be optimised for a user based on the performance of the user. Algorithms alternative to the one described above may be used without departing from this inventive principle.

For example, the ratio of sprint RPMs may be calculated for the first sprint, or at different times during the sprints. More than one ratio may be taken, and compared to more than one value, or to a parameter. The absolute change in resistance may be increased or decreased depending on which value or parameter is met by which ratio.

It will be appreciated that in certain circumstances, it will not be possible or appropriate for the control system 101 to rely on the resistance level indicator stored in the memory 107 for a particular user. This could be, for instance, that the user is new to the equipment, in particular using the equipment for the first time. Alternatively this could be because the user has not used the equipment for a prolonged period of time, such as more than a month. In such cases, the control system calculates a resistance level indicator appropriate for the user, based on the user's biometric information, in particular the user's weight.

The user may provide their biometric information in any conventional manner, such as entering it via the computing means 210 on the bike 200. Alternatively, the user may utilise biometric scales 215 to provide the data.

In the exemplary case, the weight of the user is required to establish the resistance level indicator. This is read from a look-up table that lists resistance levels by given user weight. In an example, where the apparatus is an exercise bike with resistance levels from 0-255, a suitable look-up table is:

| User Body Weight (kg) | Bike Resistance (0-255) |
|---|---|
| 20 | 66 |
| 21 | 66 |
| 22 | 66 |
| 23 | 66 |
| 24 | 66 |
| 25 | 66 |
| 26 | 66 |
| 27 | 66 |
| 28 | 66 |
| 29 | 66 |
| 30 | 66 |
| 31 | 66 |
| 32 | 66 |
| 33 | 66 |
| 34 | 66 |
| 35 | 66 |
| 36 | 66 |
| 37 | 66 |
| 38 | 66 |
| 39 | 66 |
| 40 | 66 |
| 41 | 66 |
| 42 | 66 |
| 43 | 66 |
| 44 | 66 |
| 45 | 66 |
| 46 | 66 |
| 47 | 66 |
| 48 | 66 |
| 49 | 66 |
| 50 | 67 |
| 51 | 68 |
| 52 | 69 |
| 53 | 70 |

-continued

| User Body Weight (kg) | Bike Resistance (0-255) |
|---|---|
| 54 | 71 |
| 55 | 72 |
| 56 | 73 |
| 57 | 74 |
| 58 | 75 |
| 59 | 76 |
| 60 | 77 |
| 61 | 78 |
| 62 | 80 |
| 63 | 83 |
| 64 | 85 |
| 65 | 88 |
| 66 | 90 |
| 67 | 93 |
| 68 | 95 |
| 69 | 98 |
| 70 | 100 |
| 71 | 103 |
| 72 | 105 |
| 73 | 108 |
| 74 | 110 |
| 75 | 113 |
| 76 | 115 |
| 77 | 118 |
| 78 | 120 |
| 79 | 123 |
| 80 | 125 |
| 81 | 128 |
| 82 | 130 |
| 83 | 133 |
| 84 | 135 |
| 85 | 138 |
| 86 | 140 |
| 87 | 143 |
| 88 | 145 |
| 89 | 148 |
| 90 | 150 |
| 91 | 153 |
| 92 | 155 |
| 93 | 158 |
| 94 | 160 |
| 95 | 163 |
| 96 | 165 |
| 97 | 168 |
| 98 | 170 |
| 99 | 170 |
| 100 | 170 |
| 101 | 170 |
| 102 | 170 |
| 103 | 170 |
| 104 | 170 |
| 105 | 170 |
| 106 | 170 |
| 107 | 170 |
| 108 | 170 |
| 109 | 170 |
| 110 | 170 |
| 111 | 170 |
| 112 | 170 |
| 113 | 170 |
| 114 | 170 |
| 115 | 170 |
| 116 | 170 |
| 117 | 170 |
| 118 | 170 |
| 119 | 170 |
| 120 | 170 |
| 121 | 170 |
| 122 | 170 |
| 123 | 170 |
| 124 | 170 |
| 125 | 170 |

Further biometric information may be used to establish the resistance level indicator, depending on the preferred implementation.

Give the intensity of HIT, it is preferable to provide a user who is new to the apparatus a number of initial "ramp-up" HIT protocols, to familiarise the user with the apparatus and the exercise regime without over-exerting the user. The resistance level indicator for these protocols may be lower than would ordinarily be the case according to the circumstance described above, and increased stepwise until a desired level is reached.

For instance, the processor may apply a multiplier of less than 1 to the biometric information (e.g. weight) for the first few rides, such that a user is exposed to a lower resistance level than his or her body weight would ordinarily justify. In the preferred example given below, the user's body weight is multiplied by 0.6 for the purposes of looking up the resistance level indicator from the look-up table for the first ride, and multiplied by 0.8 for the purposes of looking up the resistance level indicator from the look-up table for the second ride.

Ramp-up Ride 1:
   Resistance level indicator from look-up table as per (Body Weight×0.6)

Ramp-up Ride 2:
   Resistance level indicator from look-up table as per (Body Weight×0.8)

Ramp-up Ride 3:
   Resistance level indicator from look-up table as per (Body Weight×1.0)

Ride 4 (first ride after ramp-up)
   Resistance level indicator from look-up table as per Body Weight Following the ramp-up rides, the resistance level indicator is then algorithmically optimised after subsequent iterations of the HIT protocol, as described below.

For instance, following the system described above, a person weighing 80 kg would initially start with a resistance level indicator of 48 for the first ride, followed by a resistance level indicator of 85 for the second ride, followed by a resistance level indicator of 125 for the third and fourth rides, followed by a resistance level indicator adjusted according to the user's performance.

Since the exercise bikes 200 are intended for use without supervision, it is desirable to implement sophisticated safety monitoring routines. The exercise bike 200 and/or control system 101 according to the present invention may therefore also include real-time monitoring of the heart rate of the user during the HIT protocol. Heart rate monitoring could be performed using a chest strap or heart rate sensors build in to the equipment, as is known. Monitoring of the heart rate could take place on the exercise bike 200, or heart rate data could be transmitted from the bike 200 to the control system 101 such that monitoring can take place there.

Based on the heart rate data, the exercise apparatus 200 may stop the protocol if the heart rate falls outside predetermined thresholds, either by making such a determination itself or upon receipt of an instruction to that effect from the control system 101.

Preferably, if the starting heart rate before the first sprint, heart rate after the first sprint, or heart rate on recovery between the first and second sprints, exceeds various pre-set values described below, then the protocol is stopped. Information on the stopped protocol is also sent to the administrator of the exercise protocols and apparatus, and the user may be prevented from accessing the HIT apparatus until the administrator has allowed access.

Preferably a heart rate value is obtained once per second during the exercise.

In the exemplary protocol described above, the safety routine may operate to stop the protocol if any of the following conditions are met:

Rule 1: Staring heart rate too high
   If within the 3-minutes warm-up phase (seconds 1-180) there is at least one period of sustained heart rate of 110 or above for at least 30 seconds Rule 2: Heart rate too high after 1st sprint
   If the highest heart rate value during and after the first sprint (i.e. within first sprint and the first 30 seconds of the first recovery phase: seconds 181-230) is greater than 110% of the user's maximum heart rate for at least one period of 30 seconds Rule 3: Heart rate recovery after 1st sprint too poor
   If heart rate toward the end of the first recovery period (e.g. at second 370) is greater than 85% of the highest heart rate value in seconds 181-230 (i.e. within first sprint and the first 30 seconds of the first recovery phase)

Rule 3 only applies if the heart rate in the first recovery phase (i.e. up to 10 seconds before the second sprint starts: seconds 181 to 370) reaches 80% of the user's maximum heart rate.

For the purposes of the safety routines, the user maximum heart rate is calculated as 220 less the user's age. This may be stored in the memory 107.

Heart rate monitoring of the user may be imperfect due to the user breaking contact with the heart rate monitoring device. Therefore there may be some short gaps (a "no-val" cell), or longer gaps (a "hands-off period", or HOP), or outlier values recorded. The apparatus and methods of the invention may still function despite such breaks in heart-rate data, as heart rate values can be interpolated or approximated for these gaps. Furthermore, the heart rate may be smoothed during the protocol.

For instance, outlier values may be removed, the heart rate at a certain time may be expressed as a five-second moving average, short gaps may be filled by writing forward the value preceding the noval cell, and HOPs may be overcome by linear interpolation using the points before and after the HOP. It is important to manage the imperfect monitoring of the heart rate so that the user can be shown their heart rate without any gaps that may alarm the user. Furthermore, according to the invention, a metric may be calculated using the heart rate.

An example of a smoothing and interpolation algorithm is as follows (where 'HR(secX)' is the adjusted heart rate value at second 'X' and 'RawValueHR(secX)' is the measured heart rate value at second 'X':

Step 1: Set the first value for second 1 to 80

Step 2: Remove values which are deemed too low or too high:
   During the warm-up phase (seconds 1-180): keep only those heart rate values between 30<RawValueHR(secX)<120
   During sprint 1 and recovery phases (seconds 181-380): keep only those heart rate values between 50<RawValueHR(secX)<200
   During sprint 2 and cooldown phases (seconds 381-580): keep only those heart rate values between 50<RawValueHR(secX)<200

Step 3: Set HR(secX) according to a 5 seconds moving average:

$$HR(secX) = (RawValueHR(secX) + 5 * HR(sec(X-1)))/6$$

Step 4: Fill in short data gaps (including "no-val" cells)
For data gaps shorter than a predefined Hands-Off Period (HOP) write forward last valid HR value
HR(secX)=HR(sec(X−1) if no valid RawValueHR (secX) available Step 5: Hands-Off Periods (HOP)
Set HR(secX) to 'null' if X is within a designated HOP FIGS. 3A to 3J are screen shots showing exemplary screens visible to a user on the display 207 of the exercise bike 200 during exercise. FIG. 3A shows a log-in screen where a user is able to provide a user identifier. In conjunction with the processor, the display 207 may be further adapted to permit a user to register their details (name, email, password, age, gender etc.); administer a questionnaire to a user to determine their health status; provide instructions to users operate the apparatus, including instructions to enable a user's biometric data to be obtained (for example to weigh themselves on the biometric scale), and to receive, display, and store on the users' biometric data, either on the tablet computer or on the server to which the tablet computer is connected.

The tablet may be adapted to provide visual information on the HIT protocol being performed and the performance of the user. Such information is familiar to the skilled person, and may comprise one or a combination of: a start screen; the user's identification; a description of the different sections of the protocol; a countdown of the time left in a particular section of the protocol; a prompt to increase or decrease intensity; the user's measured heart rate; the user's measured performance parameter; and a summary upon completion of the protocol. Examples of such information are given in FIGS. 3B-3J.

As shown in FIGS. 3H and 3I, for instance, the display may be show a summary of performance data during or after the HIT exercise. The performance data may include peak heart rate, % of peak heart rate versus maximum heart rate (for example, calculated as 220 minus the user's age), maximum power output in Watts, a diagram with power output over the course of the HIT exercise, a % time the user has exercised at 90-100% of his peak power output (i.e. performance zone). Furthermore, the tablet may display a single metric designed to aid the user in comparing their performance from one iteration of an exercise protocol to another, and/or to allow users to compare themselves with each other.

The display may show a summary of performance data of all HIT exercises conducted by the user over time. The performance data may include a diagram of peak power outputs, a diagram of % time spent in performance zone, diagrams of biometric data (fat mass, muscle mass, etc).

As shown in FIG. 3J the display may show feedback questions for obtaining information relating to the user's state of tiredness, for example, and store the answers either on the tablet or on the server.

Each of the aforementioned displays may be shown sequentially (in any order) to the user, once the HIT protocol has finished.

The tablet or other computing means 210 may be adapted to provide auditory affirmations and binaural sounds via headphones to help the user relax during low intensity intervals (meditative state) and/or provide voice instructions during the HIT exercise.

Figure 5:
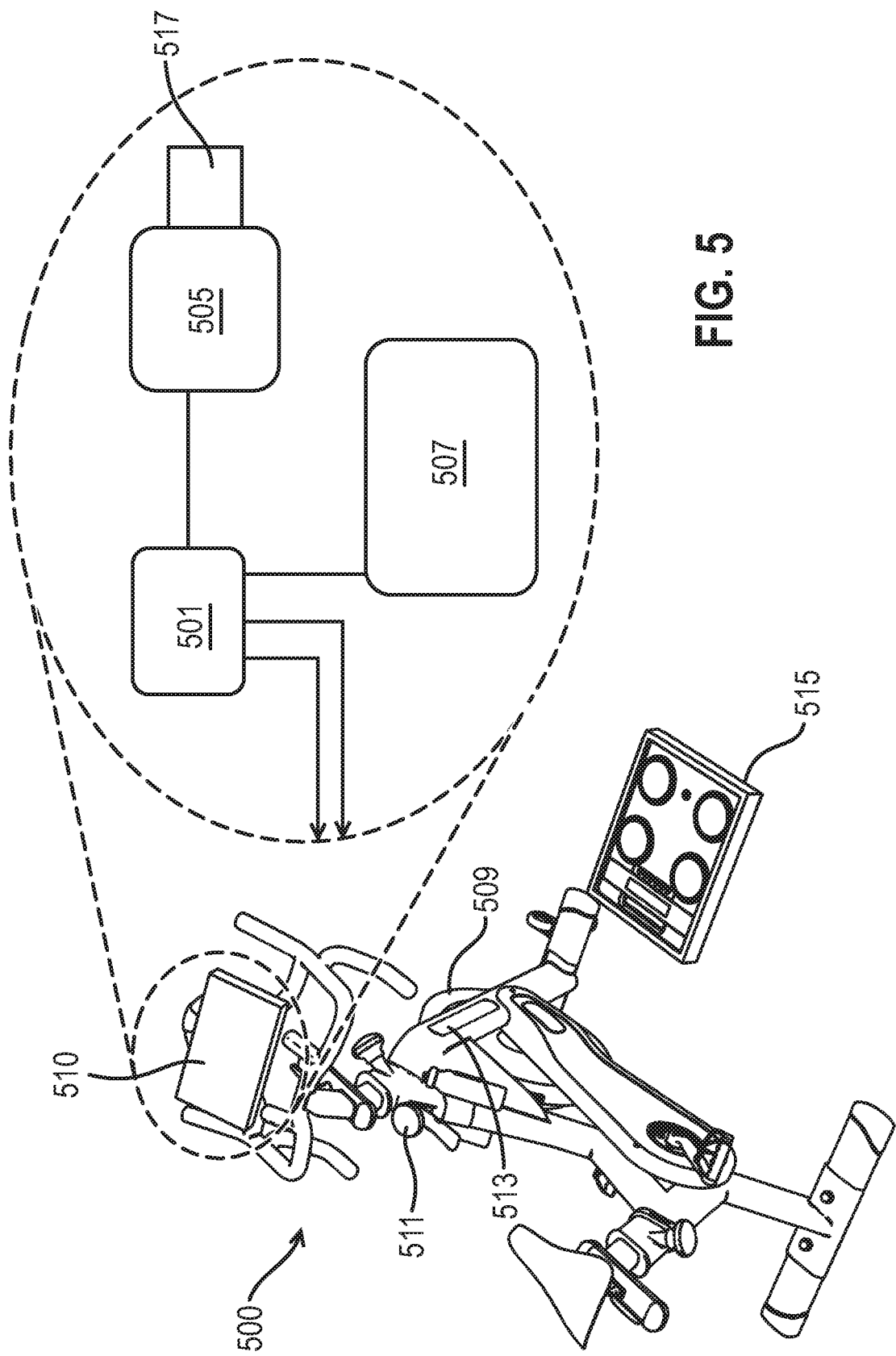
FIG. 5 shows a schematic of an exercise apparatuses according to a third aspect of the invention.

FIG. 5 shows a schematic of an exercise bike 500 according to the third aspect of the invention. The exercise bike of FIG. 5 is identical to the exercise bike of FIG. 2, except that it is capable of implementing the invention without communicating with a server.

The exercise bike comprises computing means 510 in the form of a tablet computer (although other means are possible). The tablet comprises a processor 501, a data interrogation subsystem 505 and a display 507.

As described previously with reference to the exercise bike of FIG. 2, the exercise bike of FIG. 5 further comprises a load 509 in the form of a flywheel, and a brake 511 for applying resistance to the flywheel to varying the force which the user must apply to the pedals to rotate the flywheel. The brake physically contacts the flywheel to impart resistance, but any other suitable arrangement may be provided, such as hydraulic or magnetic braking systems. Where the exercise equipment is not a bike, a skilled person will understand that equivalent loads and brakes for applying resistance to the load can be implemented.

As described previously with reference to the exercise bike of FIG. 2, the exercise bike of FIG. 5 further comprises a measurement subsystem 513 configured to measure a performance parameter of the user on the apparatus, in this case the revolutions of the flywheel or pedals per minute (RPM). Measurement of other performance parameters (such as force applied to the pedals, heart rate, etc.) is also possible.

Coupled to the computing means 510 of the bike 500 is a biometric scale 515. As described previously with reference to FIG. 2, the user's biometric information may be obtained using the scale, which may be sent to the computing means.

The data interrogation means 505 comprises a dock 517 for receiving a key fob inserted by a user with a memory containing that user's resistance level indicator. However, it will be appreciated that the resistance level indicator could take other forms. For instance, the tablet computer may be adapted to provide their resistance level indicator by the use of an RFID chip; a mobile app; a removable memory device; or any other variety of standard methods of such, as will be well understood by the skilled person.

Alternatively, the computing means itself may further comprises a memory (not shown) which stores resistance level indicators for a plurality of users in much the same way as control system 101 shown in FIG. 1. In this case, the computing means will further comprise an identification subsystem (not shown) which is configured to permit a user to provide a user identifier to log-in to the exercise bike system to begin an exercise. Users may be prompted to identify themselves by inputting a username and/or password; by the use of an RFID chip; a smartphone app; a fingerprint; a removable memory device; or any other variety of standard methods of such, as will be well understood by the skilled person and described in detail in connection with the embodiment of FIGS. 1 and 2.

As described previously with reference to the exercise bike of FIG. 2, the processor 501 of the exercise bike of FIG. 5 is coupled to the brake 511 to cause the brake 511 to apply a resistance to the flywheel 509. With the exception of safety controls such as an emergency stop, the user is unable to manually adjust the resistance applied by the brake 511 to the flywheel 509 manually or to control the processor so as to cause it to adjust the resistance. Additionally, the processor is configured to apply a resistance to prevent the bike from being operated (i.e. to prevent the flywheel from rotating) without a registered user being logged in to the system.

As described previously with reference to the exercise bike of FIG. 2, the processor 501 of the exercise bike of FIG. 5 is coupled to the measurement subsystem 513, which includes at least one sensor (not shown) for sensing RPM. For example, one or more sensors may be positioned on the frame adjacent the flywheel to sense flywheel rotation speed; one or more sensors may be positioned on the frame adjacent the pedals to sense cadence. All such sensors could be arranged by a skilled person as necessary to determine performance of the user during an exercise.

Figure 6:
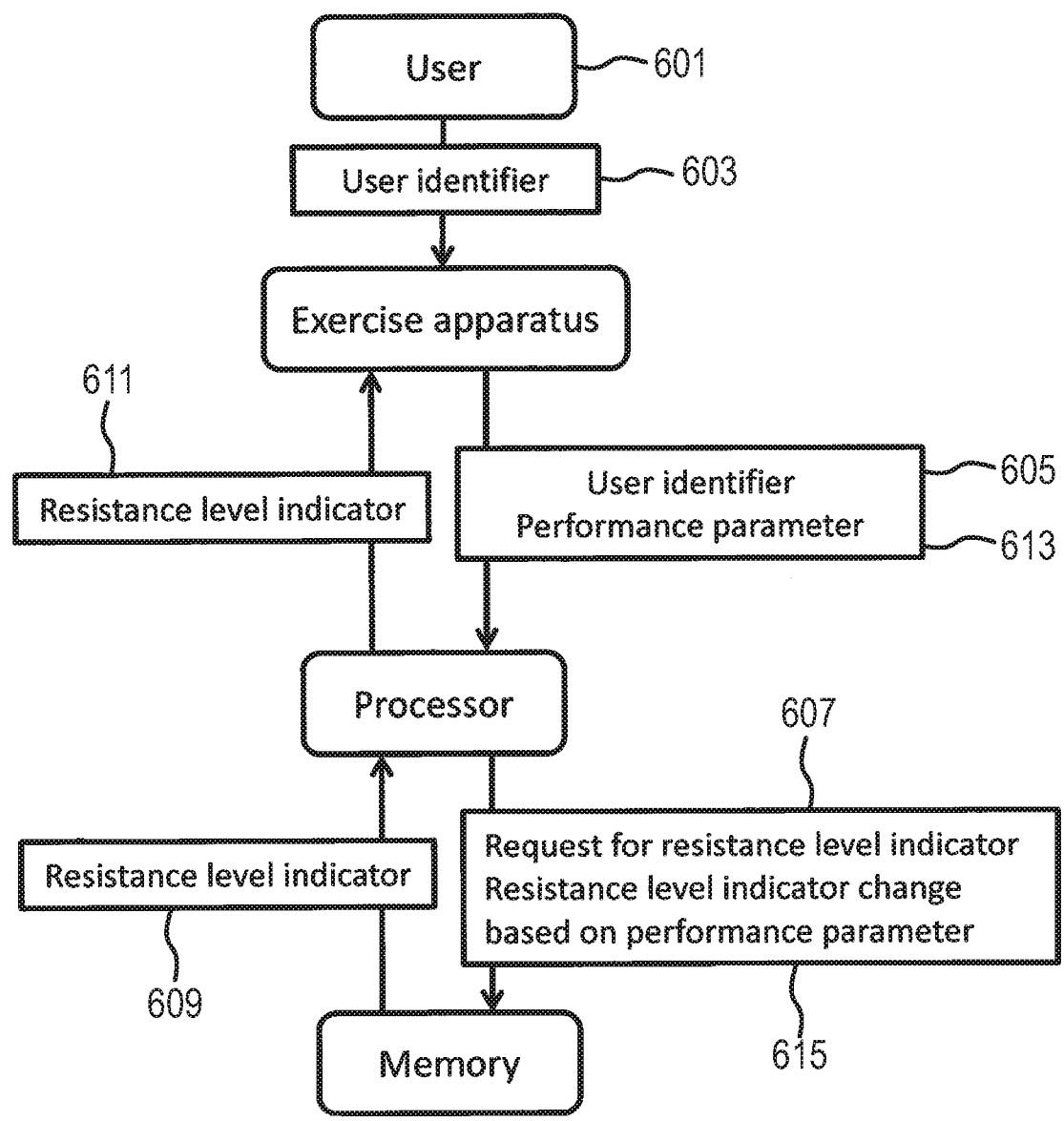
FIG. 6 shows a flow diagram of a method of operating the exercise equipment shown in FIG. 5.

In use (and with reference to the process illustrated in FIG. 6), the exercise bike 500 operates as follows. A user mounts the bike (step 601) and provides the exercise bike 600 with his or her user identifier (step 603) in the form of a key fob (not shown) inserted into the dock 517. It will be appreciated that this step is optional, however, and the user could instead simply provide a key fob (or equivalent) containing the resistance level indicator. Where a user identifier is provided, the processor 501 interrogates the fob and receives the user identifier (step 605), and then interrogates the memory (step 607) to retrieve information about the user corresponding to the user identifier. This information includes, at least, a resistance level indicator (step 609).

At some point during the user's exercise (step 611), the bike processor 501 causes the brake 511 to apply a level of resistance to the flywheel according to the resistance level indicator (as explained in more detail above in connection with the exercise bike of FIG. 2).

At some point during the user's exercise, the bike processor 501 causes the measurement subsystem to measure a performance parameter of the user, including at least the RPM (step 613).

The bike processor 501 carries out a computation (described in more detail above in connection with the exercise bike of FIG. 2) to determine whether or not to modify the resistance level indicator based on the received performance parameter. If the determination is positive, the processor modifies the resistance level indicator stored in memory (step 615), irrespective of whether the memory is within the exercise bike (and accessed using a user identifier) or provided by the user in the form of a key fob, for example.

Determination of whether to modify the resistance level indicator takes place once per exercise, and not continuously during the exercise. Thus, where the resistance level indicator stored in memory is modified based on the performance parameter measured during one exercise, the modified resistance level indicator will be used to set the resistance applied by the brake for the next exercise.

In all other respects (in particular with reference to the protocols and algorithms for determining whether or not to modify the resistance level indicator), the exercise bike of FIG. 5 operates the same as the control system and exercise bike of FIGS. 1 and 2, except that all processing takes place at the bike, rather than across a distributed network.

Figure 7:
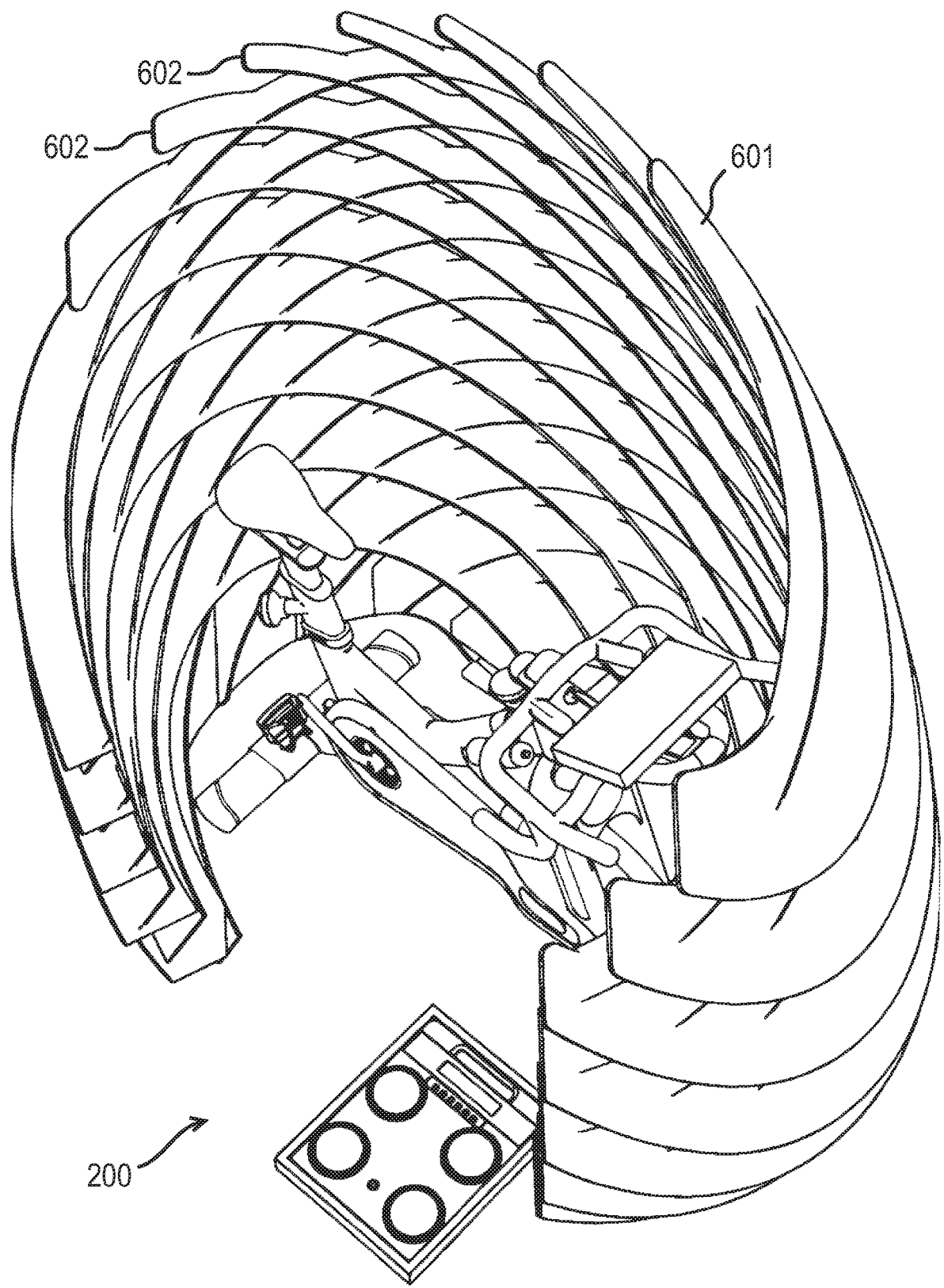
FIG. 7 shows the exercise apparatus shown in FIG. 6 partially enclosed by a screen.

FIG. 7 shows an exercise bike 200 further comprising a screen 601 at least partially enclosing the bike. HIT requires users to exercise at their peak performance levels. The screen 601 enables HIT to be much more accessible and convenient for a broad range of users. In particular, the screen 601 enables exercise bikes to be placed in lobbies and cafeterias of office buildings, for example, or in public areas in retail outlets and shopping centres, for example, or other similarly public places.

The screen 601 comprises a plurality of slats 602 interconnected to form a free-standing structure which mostly (i.e. at least partially) surrounds the exercise bike 200. At least some of the slats are oriented at an angle to the horizontal, so as to at least partially block a bystanders view of the user and exercise apparatus. However, in other embodiments the screen may be any structure capable of at least partially concealing a user and the exercise apparatus.

The screen 601 provides users with a minimum level of privacy, and which has been specifically designed to minimise the space requirement/footprint of the system. The screen 601 may be equipped with a number of additional features, such as an integrated ventilation and cooling system, an integrated biometric scale, integrated user interfaces such as a display (as an alternative to the display attached to the exercise bike directly), a smartcard or keyfob reader, a surveillance and alarm system, which together with the flywheel locking mechanism, all of which are described above. The screen would thus give our system multiple-user capabilities for unsupervised use in public areas.

Accordingly to the above, this invention provides for exercise apparatus and control systems thereof that are specifically designed to make it easier for a user to correctly carry out an HIT protocol. The user only has to identify themselves, and then focus on performing the HIT protocol correctly. The resistance level for the individual user during the high intensity sections of the HIT protocol is optimised such that the user is working at the correct intensity, enabling the user to see the full benefit of this form of exercise. This is achieved by algorithmically optimising the resistance level over time, using the measured performance parameter of the user as the input. This mean that the user is working at or near their maximum power output, and the resistance level will self-adjust as the fitness level of the user changes.

While certain preferred embodiments of the invention have been described here, it will be apparent that modifications and variations of these embodiments may be made without changing the scope of the invention.

The invention claimed is:

1. A control system for controlling one or more of a plurality of exercise apparatuses across a network, each of the plurality of exercise apparatuses comprising a brake for applying resistance and being configured to transmit a user identifier and a performance parameter of a user, the control system comprising:

a processor;

a communication subsystem configured to communicate with the plurality of exercise apparatuses across the network; and a memory for storing information about one or more users, the information comprising, for each user:

identity information, including a user identifier;

weight; and a resistance level indicator;

wherein upon receipt of a user identifier from one of the one or more of the plurality of exercise apparatuses in the network, the processor is configured to identify a resistance level indicator stored in the memory corresponding to the user identifier;

wherein, if the user is using the one or more of the plurality of exercise apparatuses for the first time, the processor is configured to set the resistance level indicator appropriate for the user based on the user's weight;

wherein the processor is configured to cause the communication subsystem to transmit the resistance level indicator for that user to the one of the one or more of the plurality of exercise apparatuses in order that a resistance is applied by a brake of the one of the one or more of the plurality of exercise apparatuses according to the resistance level indicator, wherein the resistance applied by the brake during exercise is controllable only by the resistance level indicator stored in the memory, and wherein the resistance applied by the brake during exercise is not adjustable by the user during exercise;

wherein upon receipt of a performance parameter of the user measured on the one of the one or more of the plurality of exercise apparatuses during the user's exercise in the network, the processor is configured to determine, based on the received performance parameter, whether or not to modify the resistance level indicator of that user stored in the memory;

wherein, if the determination is positive, the processor is configured to modify the resistance level indicator stored in the memory, wherein the modified resistance level indicator will be used to set a resistance applied by a brake of one of the one or more of the plurality of exercise apparatuses for a next exercise.

2. The control system of claim 1, wherein the processor is further configured to set the resistance level indicator of the user based on the user's weight according to a look-up table.

3. The control system of claim 1, wherein the information about one or more users further comprises, for each user, a counter indicative of the number of exercises completed by the user; optionally
 wherein the processor is configured to set the resistance level indicator of the user based on the user's weight only when the counter is equal to or below a threshold value; optionally
 wherein the threshold value is 2.

4. The control system of claim 2, wherein the processor is configured to apply a multiplier to the weight according to the value of the counter; optionally
 wherein the processor is configured to:
 apply a multiplier of 0.6 to the weight when the counter is equal to 0; and/or
 apply a multiplier of 0.8 to the weight when the counter is equal to 1; and/or
 apply a multiplier of 1 to the weight when the counter is equal to 2.

5. The control system of claim 1, wherein the processor is further configured to transmit to the one of the one or more of the plurality of exercise apparatuses instructions for implementing an exercise protocol, wherein the protocol comprises a plurality of periods including first and second sprint periods; optionally
 wherein the protocol comprises applying at least two different resistance levels during the plurality of periods.

6. The control system of claim 5, wherein the protocol consists of:
 a warm up period, followed by
 a first sprint period, followed by
 a first recovery period, followed by
 a second sprint period, followed by
 a second recovery period; optionally
 wherein:
 the duration of the warm-up period is 180 seconds;
 the duration of the first sprint period is 20 seconds;
 the duration of the first recovery period is 180 seconds; and/or
 wherein the resistance level applied during the first and/or second sprint periods is based on the resistance level indicator.

7. The control system of claim 6, wherein:
 a first resistance level is applied during the warm up period;
 a second resistance level is applied during the first sprint period;
 the first resistance level is applied during the first recovery period;
 the second resistance level is applied during the second sprint period; and
 the first resistance level is applied during the second recovery period; optionally
wherein the first resistance level is the lowest resistance setting of the one of the one or more of the plurality of exercise apparatuses.

8. The control system of claim 1, wherein the performance parameter is a ratio of a first performance measurement to a second performance measurement, wherein the first and second performance measurements are taken at different times during an exercise.

9. The control system of claim 8, wherein the first performance measurement is taken before the second performance measurement.

10. The control system of claim 9, wherein wherein the first and second performance measurements are taken during the second sprint period; optionally
 wherein the first performance measurement is taken 5 seconds into the second sprint period; and/or
 wherein the second performance measurement is taken 15 seconds into the second sprint period.

11. The control system of claim 1, wherein the processor is further configured to compare the received performance parameter with one or more threshold values to determine whether or not to modify the resistance level indicator Optionally
 wherein the processor is further configured to compare the received performance parameter with an upper threshold value, and to increase the resistance level indicator if the received performance parameter exceeds the upper threshold values; and/or
 wherein the processor is further configured to compare the received performance parameter with a lower threshold value, and to decrease the resistance level indicator if the received performance parameter is below the lower threshold value; and/or
 wherein the processor is further configured to compare the received performance parameter with an upper threshold value and a lower threshold value, and to maintain the resistance level indicator if the received performance parameter is between the upper and lower threshold values.

12. The control system of claim 1, wherein upon reaching the determination to modify the resistance level indicator, the processor is configured to modify the resistance level indicator by a predetermined amount.

13. The control system of claim 12, wherein one of the one or more of the plurality of exercise apparatuses is an exercise bike, and wherein the performance parameter is revolutions per minute RPM.

14. A method for controlling one or more of a plurality of exercise apparatuses across a network, each of the plurality of exercise apparatuses comprising a brake for applying resistance, the method comprising:
 receiving a user identifier of a user from one of the one or more of the plurality of exercise apparatuses;
 retrieving a resistance level indicator corresponding to the user identifier from a memory;
 if the user is using the one or more of the plurality of exercise apparatuses for the first time, setting the resistance level indicator appropriate for the user based on the user's weight;
 transmitting the resistance level indicator to the one of the one or more of the plurality of exercise apparatuses in order that a resistance is applied by a brake of the one of the one or more of the plurality of exercise apparatuses according to the resistance level indicator, wherein the resistance applied by the brake during exercise is controllable only by the resistance level indicator, and wherein the resistance applied by the brake during exercise is not adjustable by the user during exercise;

receiving a performance parameter of the user measured on the one of the one or more of the plurality of exercise apparatuses;

determining, based on the received performance parameter, whether or not to modify the resistance level indicator; and, if the determination is positive:

modifying the resistance level indicator corresponding to the user identifier in the memory, wherein the modified resistance level indicator will be used to set a resistance applied by a brake of one of the one or more of the plurality of exercise apparatuses for a next exercise.

15. An exercise apparatus and a control system, wherein the exercise apparatus is controlled by the control system, wherein the control system is as defined of claim 1, wherein the exercise apparatus is configured to communicate with the control system across a network, the control system being configured to transmit a resistance level indicator indicative of a resistance level to be applied by the exercise apparatus, the exercise apparatus comprising:

a processor;

a communications subsystem configured to communicate with the control system across the network;

an identification subsystem configured to receive a user identifier from a user;

a load for use in exercise and a brake for applying resistance to the load; and a measurement subsystem configured to measure a performance parameter of the user on the apparatus;

wherein upon receipt of a user identifier from a user, the processor is configured to cause the communication subsystem to transmit the user identifier to the remote server across the network;

wherein upon receipt of a resistance level indicator from the control system, the processor is configured to cause the brake to apply a corresponding resistance to the load, wherein the resistance applied by the brake during exercise is not adjustable by the user and wherein the resistance applied by the brake during exercise is controllable only by the received resistance level indicator; and wherein upon measurement of a performance parameter of the user on the apparatus, the processor is configured to cause the communication subsystem to transmit to the control system the performance parameter of that user.

* * * * *